(12) United States Patent
Lehmann et al.

(10) Patent No.: US 9,814,653 B2
(45) Date of Patent: *Nov. 14, 2017

(54) HOME MEDICATION MANAGER

(71) Applicants: The Research Foundation for The State University of New York, Albany, NY (US); Chang Hong Chen, Stony Brook, NY (US); Tim Kehoe, Smithtown, NY (US); Robert Barnikel, Fort Salonga, NY (US)

(72) Inventors: Craig Lehmann, Aquebogue, NY (US); John Brittelli, Brookhaven, NY (US); Chang Hong Chen, Stony Brook, NY (US); Tim Kehoe, Smithtown, NY (US); Robert Barnikel, Fort Salonga, NY (US)

(73) Assignee: The Regents Foundation for The State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,151

(22) Filed: Dec. 21, 2016

(65) Prior Publication Data

US 2017/0128326 A1 May 11, 2017

Related U.S. Application Data

(63) Continuation of application No. 14/789,000, filed on Jul. 1, 2015, now Pat. No. 9,554,969, which is a (Continued)

(51) Int. Cl.
*A61J 7/04* (2006.01)
*G09B 5/02* (2006.01)
*G06F 19/00* (2011.01)

(52) U.S. Cl.
CPC .......... *A61J 7/0436* (2015.05); *A61J 7/0418* (2015.05); *A61J 7/0454* (2015.05); *A61J 7/0481* (2013.01);
(Continued)

(58) Field of Classification Search
CPC ....... A61J 7/0481; A61J 7/0084; A61J 7/0454
See application file for complete search history.

(56) References Cited

U.S. PATENT DOCUMENTS

| 4,275,384 A | 6/1981 | Hicks et al. |
| 5,088,056 A | 2/1992 | McIntosh et al. |

(Continued)

OTHER PUBLICATIONS

"How It Works? Automatic Pill Dispenser", website—http://www.epill.com/medtimeclosed.html (3 pages) (Aug. 11, 2014).
(Continued)

*Primary Examiner* — Timothy Waggoner
(74) *Attorney, Agent, or Firm* — Scully, Scott, Murphy & Presser, P.C.

(57) ABSTRACT

A portable self medication management system and method of provided. For example, the system may include a removable tote and docking station. The removable tote including a plurality of receptacles, communicating section for transferring data to and from a docking station and a power reception station for receiving power from the docking station. The docking station including a scanner, a display screen, a controller, a storage device, communicating sections for transmitting data to the removable tote and other external devices and a power transmitting section for transferring power to the removable tote.

20 Claims, 24 Drawing Sheets

Related U.S. Application Data continuation-in-part of application No. 14/448,104, filed on Jul. 31, 2014, now Pat. No. 9,498,408, which is a continuation-in-part of application No. PCT/US2014/025479, filed on Mar. 13, 2014.

(60) Provisional application No. 61/888,764, filed on Oct. 9, 2013, provisional application No. 61/783,798, filed on Mar. 14, 2013.

(52) U.S. Cl.
CPC ........... *G06F 19/3462* (2013.01); *G09B 5/02* (2013.01); *A61J 2200/30* (2013.01); *A61J 2205/10* (2013.01); *A61J 2205/20* (2013.01); *A61J 2205/30* (2013.01); *A61J 2205/60* (2013.01); *A61J 2205/70* (2013.01)

(56) References Cited

U.S. PATENT DOCUMENTS

| | | | |
|---|---|---|---|
| 5,099,463 | A | 3/1992 | Lloyd et al. |
| 5,181,189 | A | 1/1993 | Hafner |
| 5,239,491 | A | 8/1993 | Mucciacciaro |
| 5,564,593 | A | 10/1996 | East, Sr. |
| 5,669,503 | A | 9/1997 | Robin |
| 5,713,485 | A | 2/1998 | Liff et al. |
| 5,774,865 | A | 6/1998 | Glynn |
| 5,915,558 | A | 6/1999 | Girvetz |
| 5,954,225 | A | 9/1999 | Powe |
| 6,021,902 | A | 2/2000 | Wu |
| 6,294,999 | B1 | 9/2001 | Yarin et al. |
| 6,539,281 | B2 | 3/2003 | Wan et al. |
| 7,072,738 | B2 | 7/2006 | Bonney et al. |
| 7,170,823 | B2 | 1/2007 | Fabricius et al. |
| 7,269,476 | B2 | 9/2007 | Ratnakar |
| 7,299,981 | B2 | 11/2007 | Hickle et al. |
| 7,369,919 | B2 | 5/2008 | Vonk et al. |
| 8,019,471 | B2 | 9/2011 | Bogash et al. |
| 8,045,420 | B2 | 10/2011 | Newman |
| 8,108,068 | B1 | 1/2012 | Boucher et al. |
| 8,391,104 | B2 | 3/2013 | de la Huerga |
| 9,072,654 | B2 | 7/2015 | Pentz |
| 9,498,408 | B2 | 11/2016 | Lehmann et al. |
| 9,554,969 | B2 * | 1/2017 | Lehmann ............ G06F 19/3462 |
| 2006/0241355 | A1 | 10/2006 | Howell et al. |
| 2009/0259336 | A1 | 10/2009 | Ratnakar |
| 2012/0154120 | A1 | 6/2012 | Alloro et al. |
| 2013/0024022 | A1 | 1/2013 | Bowers |
| 2013/0110283 | A1 | 5/2013 | Baarman et al. |
| 2014/0310018 | A1 | 10/2014 | Cizmarik |
| 2014/0350720 | A1 | 11/2014 | Lehmann et al. |
| 2015/0317455 | A1 | 11/2015 | Lehmann et al. |
| 2016/0015602 | A1 | 1/2016 | Panzini et al. |

OTHER PUBLICATIONS

"Remote Medication Management System—The Official Site of InRange Systems™", website—http://www.inrangesystems.com/remote-medication-management-system/ (5 pages) (Aug. 11, 2014).

"Reduce the Risk of Medication Errors With the Philips Medication Dispensing Service", website—http://www.vnacares.org/assets/files/Programs/Lifelines/Philips_Medication_Disepenser.pdf (2 pages) (Aug. 11, 2014).

International Search Report and Written Opinion dated Jul. 31, 2014 received from the International Searching Authority from related Application No. PCT/US2014/025479.

International Search Report and Written Opinion dated Oct. 30, 2015 received from the International Searching Authority from International Application No. PCT/US15/42762.

U.S. Final Office Action dated Jul. 12, 2016 received in U.S. Appl. No. 14/789,000.

U.S. Office Action dated Mar. 18, 2016 received in U.S. Appl. No. 14/789,000.

U.S. Office Action dated Mar. 1, 2016 received in U.S. Appl. No. 14/448,104.

\* cited by examiner

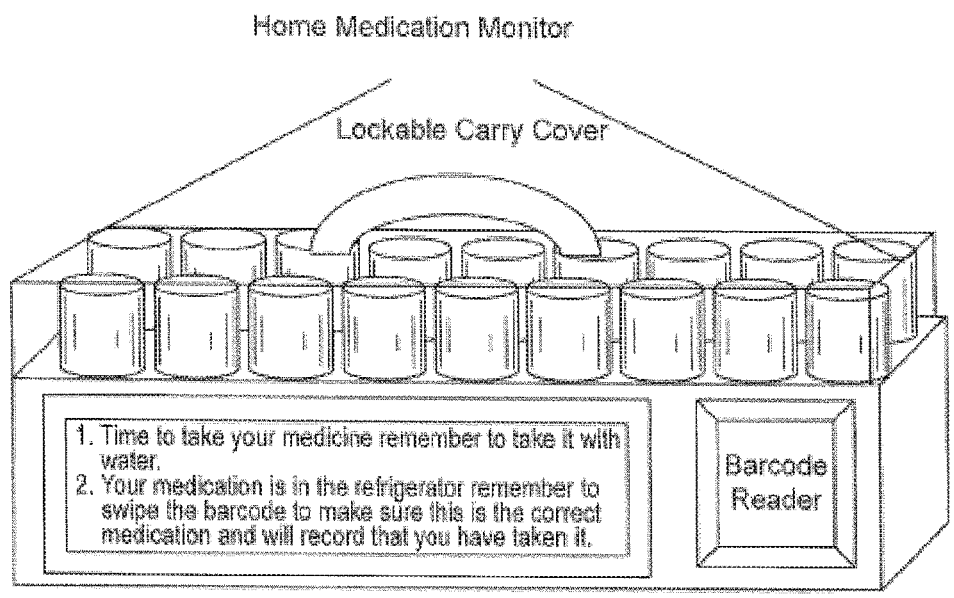
FIGURE 8
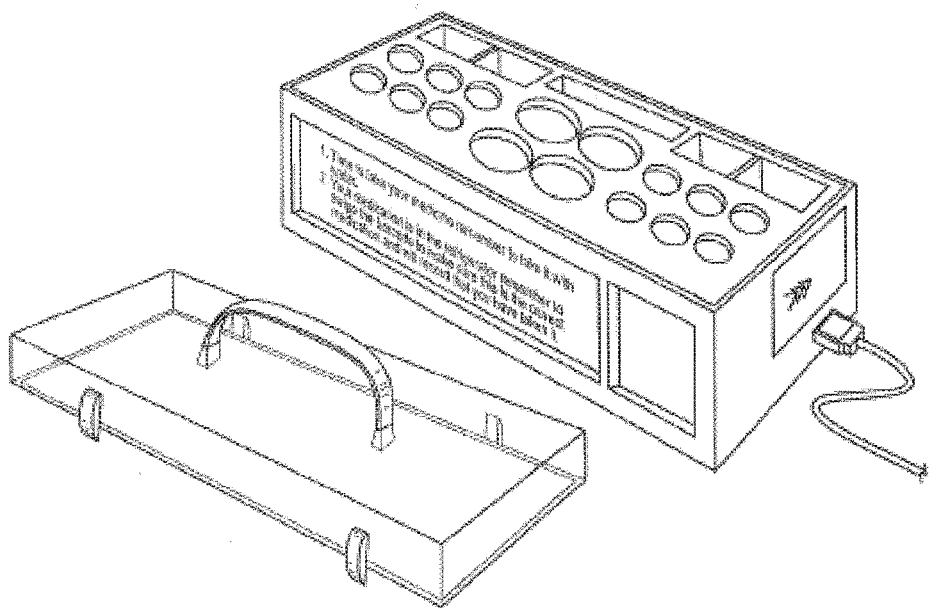

HOME MEDICATION MANAGER

CROSS REFERENCE TO RELATED APPLICATIONS

The present application is a continuation of co-pending application having U.S. Ser. No. 14/789,000, filed Jul. 1, 2015, which is a continuation in-part of application having U.S. Ser. No. 14/448,104, filed Jul. 31, 2014, now U.S. Pat. No. 9,498,408, which is a continuation in-part of PCT Application No. PCT/US2014/025479, filed on Mar. 13, 2014, which claims benefit of U.S. Provisional Application No. 61/888,764, filed Oct. 9, 2013 and U.S. Provisional Application No. 61/783,798, filed Mar. 14, 2013, the entire contents of which are incorporated herein by reference.

FIELD OF THE INVENTION

The present disclosure relates generally to medication management, and in particular to a home self medication management method, system and apparatus which monitors medication administration including dosage and timing. More specifically, certain aspects of the instant disclosure describe a home medication manager that includes a base housing that includes a removable tote portion having a plurality of medication holders or receptacles for receiving and holding numerous medications and a docking station within which the removable tote portion sits.

BACKGROUND

Often it is difficult for a patient to remember to take prescribed medication. This can be especially true for patients who are prescribed multiple medications that need to be taken at different frequencies and times of day. This problem can be compounded by patient confusion, reduced short-term memory, etc. Missing a dose of medication, accidently taking a pill twice, and/or adverse interaction between prescribed medications are all significant causes of adult visits to emergency rooms. For example, according to data reported by Medicare, heart failure patients were prescribed an average of twelve (12) medications, and some were prescribed as many as thirty (30) different types of medication. With half of these medications taken 2 or 3 times per day, this amounts to over 100 pills per day, all needing to be coordinated to be taken at specific times and following specific instructions, such as taken with meals, with water, while fasting, etc. In the year 2000, the costs of medication-related morbidity in ambulatory care setting exceeded $177.4 billion. Moreover, lack of medication compliance after discharge from the hospital is a primary reason for patients being re-admitted.

Because of these issues and others, it is imperative that today's technology provide appropriate clear directions on when a particular medication is needed and how it is to be taken (e.g. with food and/or water). Hence there is a need for portable home medication reminders, medication dispensers and devices that combine informing and dispensing functions that can help patients manage their medications and reduce the risk that a patient will miss taking his medication in the home or while traveling. Moreover, home medication management systems that provide guidance and maintain the integrity of the original packaging will limit the potential for a user to take a prescribed medication inadvertently, which may increase the possibility of adverse effects caused by such a medication.

SUMMARY OF THE DISCLOSURE

A novel system, method and apparatus, e.g., "home medication manager" or "home medication management system", for medication management is presented. The instant apparatus can serve as a home base medication manager and also can be transported anywhere at any time simply by unplugging it. Additionally, in certain aspects of the present disclosure a patient can take a necessary amount of prescribed medication while traveling outside the home by using the compact electronic medication box component of the home medication manager. In certain embodiments, the home medication manager can provide both verbal and visual instructions for accurate self medication management. In one embodiment, the home medication manager can obtain all the necessary information and/or instructions for daily consumption of an individual's medication from a descriptive barcode provided on the original container supplied by the pharmacist (local or mail order). In another embodiment, information can be obtained from user input. One embodiment comprises a variety of medication holders, for example a total of twenty (20), that accommodate different sizes of original medication containers including containers for pills, for liquids and/or foil containers, e.g., blister packs.

An embodiment of the present disclosure includes a system comprising: a base comprising a plurality of receptacles, each receptacle having a sensor, a visual indicator, and a securing mechanism, the system further comprising a scanner, a display screen, a power source, a memory device, a storage device, and a hardware processor coupled to the memory device and couple-able to the storage device, the processor configured to acquire, using the scanner, medication information from a medication container holding a medication, the medication information comprising at least an administration time; the processor further configured to determine whether the medication information exists in a first database residing on the storage device, if the medication information does not exist in the first database, to associate the medication information with a location information comprising at least a receptacle and store the medication information and the location information in the first database, to indicate, using the receptacle visual indicator, the location information, and confirm, using the receptacle sensor, placement of the medication container in the associated receptacle in accordance with the securing mechanism, notify a user to administer the medication held in the medication container based on the administration time, and request the user to scan, at the scanner, the medication container of the notified medication, to detect, based on the scan of the medication container, retrieval of an incorrect medication container from the plurality of receptacles, and issue a warning of the detection, and to provide instructions on the display screen for administering the medication, the instructions based on the medication information.

An embodiment of the present disclosure performs the steps of: acquiring medication information from a medication container holding a medication, the medication information comprising at least an administration time, determining whether the medication information exists in a first database residing on a storage device, if the medication information does not exist in the first database, associating the medication information with a location information comprising at least a receptacle having at least a visual indicator, a sensor and a securing mechanism, and storing the medication information and the location information in the first database, indicating, using the receptacle visual indicator, the location information, and confirming, using the receptacle sensor, placement of the medication container in the associated receptacle in accordance with the securing mechanism, notifying a user to administer the medication held in the medication container based on the administration time, and requesting the user to scan, at the scanner, the medication container of the notified medication, detecting, in accordance with the scanner, retrieval of an incorrect medication container, and issuing a warning of the detection, and providing instructions on the display screen for administering the medication, the instructions based on the medication information.

In one aspect of the present disclosure, the medication management system integrates a small (e.g., 2.5×5 inch or 2×3 inch) portable, compact electronic box, which allows an individual to travel with needed medication (e.g., four-six doses) over a 24 hour period. In certain embodiments, the home medication manager can prompt the user to separate needed medication into at least four (4) different time periods by illuminating those medications that will need to be taken at each time period. For example, the home medication manager can direct the individual to place particular pills in compartment "A" and set the "A" timer alarm for a given time, e.g., the initial time of the "A" time period. All of the medications for compartment "A" will be lit and, after the required medications are removed from their respective containers and the containers placed back in the system, the light and/or notification will shut off. This process is repeated for any additional compartments, e.g., compartments "B, C" and "D". Once all individual compartments have been populated with the appropriate medication(s), the time alarms are set for each compartment and the individual can go out. When it is time to take pills in the compact electronic box, the individual compartment (e.g., A, B, C, D, E) can illuminate, vibrate or provide notification to the user and/or the wrist band and/or pendant can alert the user that it is time to take the prescribed medication(s). The process repeats until all time periods have passed.

In yet another embodiment of the present disclosure, the medication management system includes a base unit including a removable tote portion and a docking portion, whereby the removable tote portion of the base includes a plurality of receptacles, each receptacle having a sensor, a visual indicator, and/or a means for securing a medication. In certain embodiments the removable tote portion includes a radio-frequency identification tag (RFID), which identifies and tracks the removable tote associated with a corresponding docking portion of a base unit. In other embodiments the removable tote portion includes a means for transferring data and a means for receiving power from the docking portion. In specific embodiments data is transferred between the docking station and the removable tote through psychical contacts, such as a two-way data port, electrical contacts that complete a circuit between the docking station and removable tote portion, a wireless data antenna and receiver, a wireless power antenna and receiver, an RFID chip and an RFID reader, or a combination thereof. In certain embodiments, the removable tote portion of the base unit includes a microcontroller, non-volatile memory unit for facilitating communication between elements of the removable tote portion.

A computer readable storage medium storing a program of instructions executable by a machine to perform one or more methods described herein also is also provided.

BRIEF DESCRIPTION OF THE DRAWINGS

These and other features, aspects, and advantages of the present invention will become better understood with regard to the following description, appended claims, and accompanying drawings wherein:

FIGS. 5-8 illustrate aspects of embodiments of the present disclosure.

DETAILED DESCRIPTION

Figure 1:
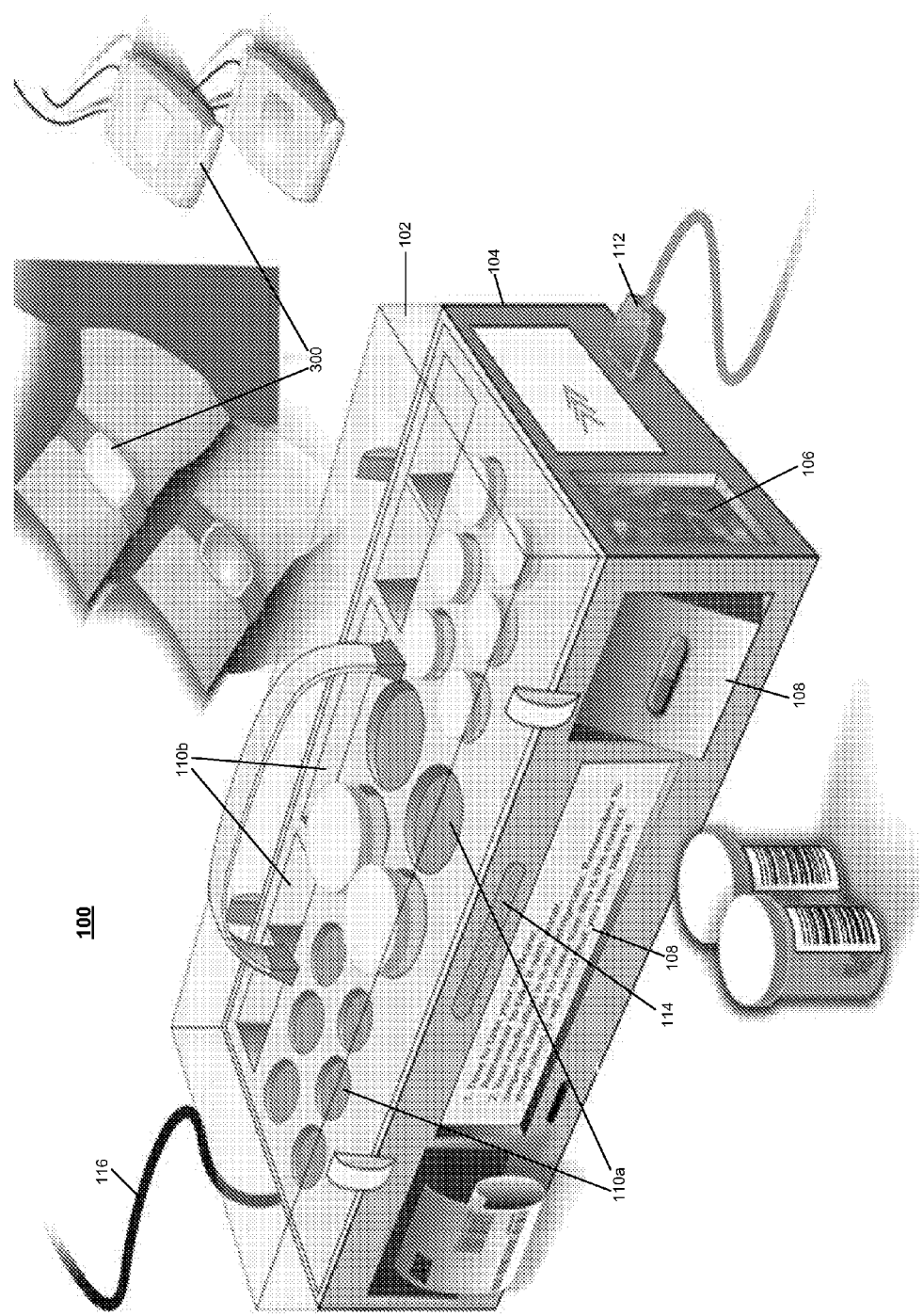
FIG. 1 illustrates an embodiment of the present disclosure.
Figure 2:
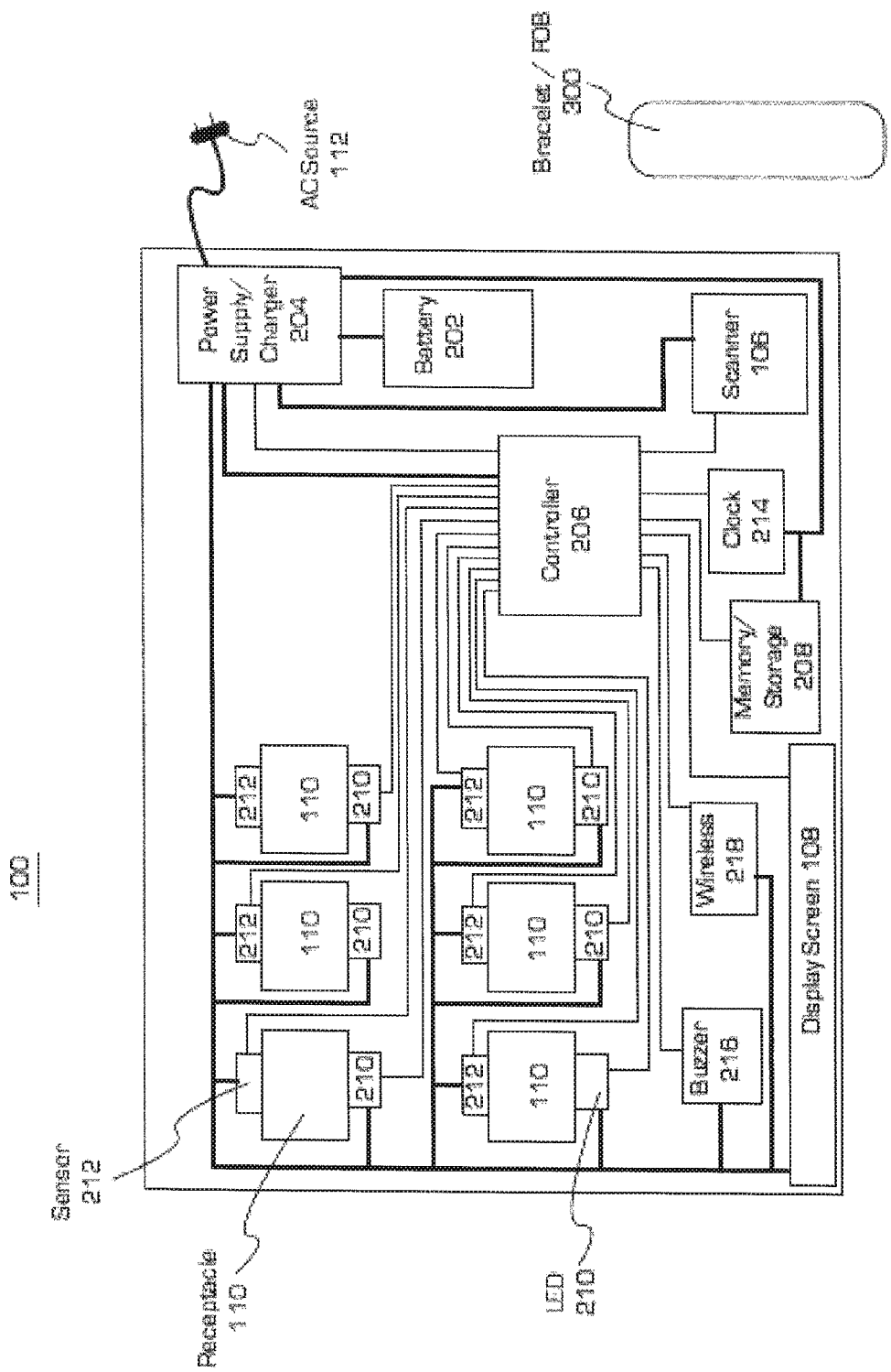
FIG. 2 illustrates a Hock representation of an embodiment of the present disclosure.

FIG. 1 illustrates an embodiment of the present disclosure in which a home medication manager 100 comprises a portable medication storage and management apparatus. FIG. 2 illustrates a block representation of an embodiment of the home medication manager 100. The home medication manager 100 includes a locking lid 102 and a base housing 104. A barcode reader or scanner 106 is provided on an outside surface of the base housing 104. Additionally, the base housing 104 includes at least one display screen 108 on an outside surface. A top surface of the base housing 104 can be formed into a plurality of medication holders or receptacles 110. The base housing can further include at least one speaker and microphone element 114, which can be used to provide voice prompts and/or notifications to or from the home medication manager.

A scanner 106 may be configured to read one or more of Universal Product Code indicia (UPC), Quick Response (QR) code, high capacity color barcode (HCCB) from a medication container. In another embodiment, the scanner 106 can be configured to read unpowered near-field communication (NFC) tags provided on a medication container. The UPC indicia may be used to identify the individual medication held within the medication container. The more data-dense indices, such as QR, HCCB and NFC tags, may contain medication related information, such as dosage instructions, expiration date, remaining refills, and interaction information. In one embodiment, the scanner 106 can be a barcode reader which will be capable of reading both three-dimensional and two-dimensional barcodes. When a patient receives a new medication or a refill/renewal, the patient will scan the barcode located on the original medication container of the new or refill medication. The home medication manager 100 can determine from the scanned barcode information whether the original medication container contains a new medication or a refill. Then the home medication manager 100 can assign a new receptacle 110, e.g., location, if it is a new medication or the same receptacle, e.g., location, as the previous original medication container if the medication is a refill or renewal.

Figure 10:
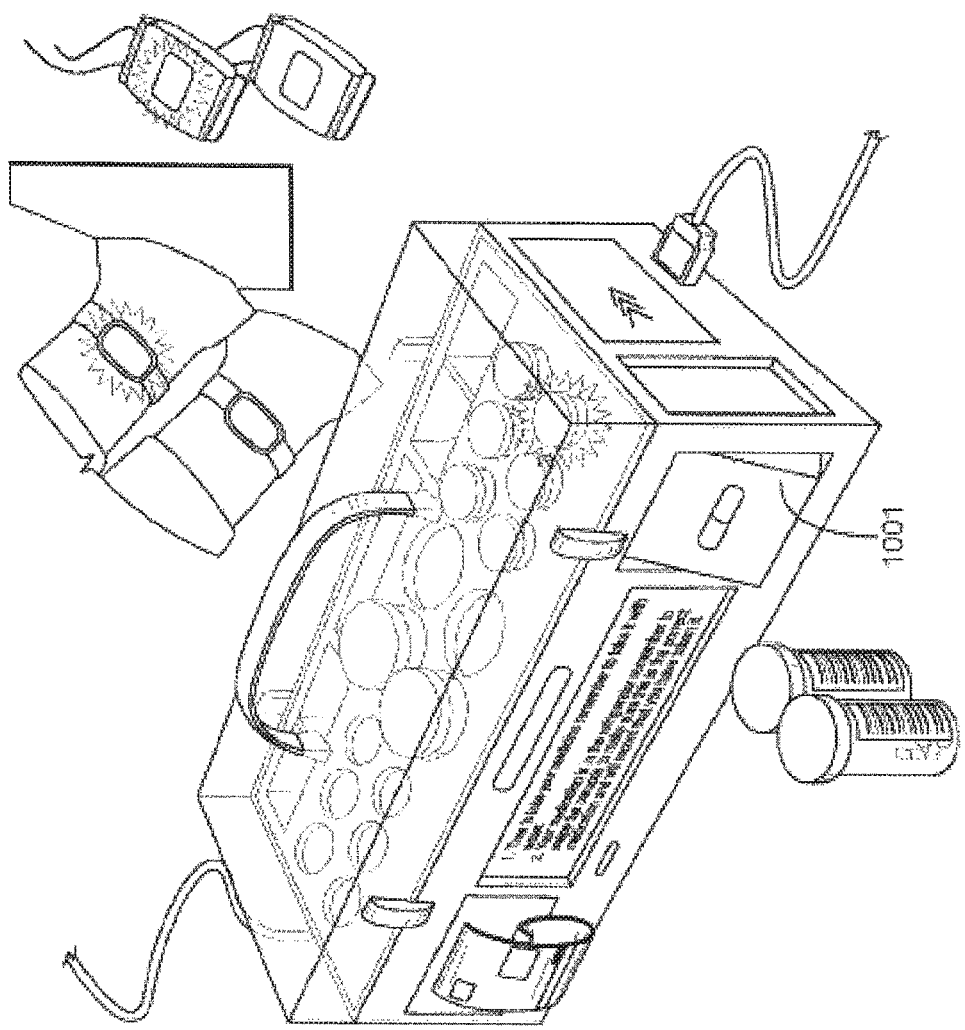
FIGS. 10-13 illustrate additional aspects of embodiments of the present disclosure.
Figure 11:
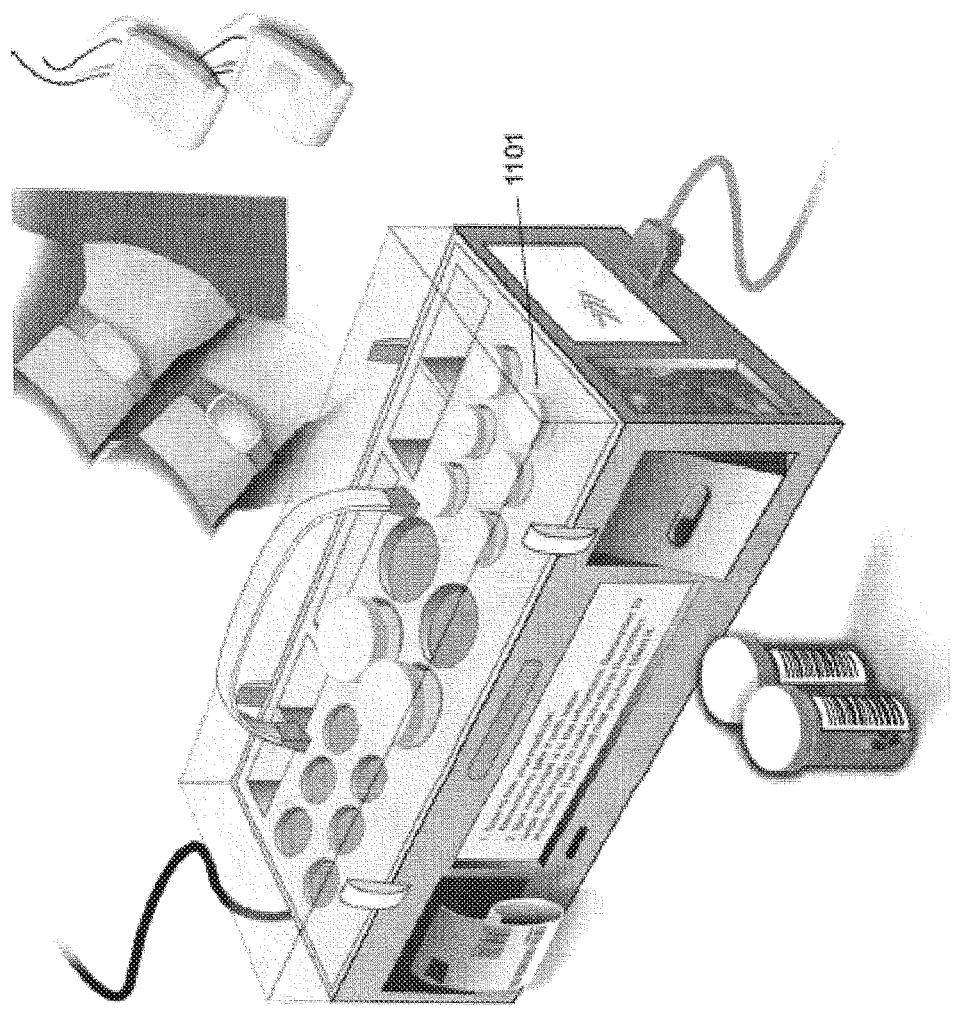

A display screen 108 may be a liquid crystal display (LCD), an e-paper/e-ink display, or an organic LED (OLED) display, or other displays as known to one skilled in the art. The display screen 108 can function to provide usage instructions to the patient, as well as alerts, such as time to take a medication, expiration of a medication, warnings, etc. The display screen 108 can also be equipped with a touch sensitive interface that enables user interaction between the home medication manager 100 and the patient. For example, the patient/user can input information related to a scanned medication by way of the touch interface when prompted on the display screen 108. In one embodiment, a second display screen 1001, as shown in FIG. 10, can be placed on an outer surface of the base housing 104. This second display screen 1001 can be a high density color LCD display or LED panel capable of displaying at least an image of the medication, e.g., a pill, that the patient is scheduled to take, so that the patient can be assured that he is taking the correct pill. In certain embodiments, the second display screen 1001 will provide the user with an image of the medication and unique indentifying characteristics of the medication that the patient is scheduled to take; so that the patient can be assured that they are taking the correct medication. In certain non-limiting examples, such identifying characteristics include shape of the medication (e.g., oval), color (e.g., white, orange, blue), markings (i.e., the letter V, the number 3, etc.).

In a specific embodiment of the present disclosure, the patient is notified by the home medication manager that it is time to take medication. The slot containing the medication due to be taken is illuminated or otherwise indicated, for example, through communication between the sensor and controller. The patient removes the bottle of medication and removes one of the pills. Concurrently and the image of the pill is displayed on the display screen 1001 and/or 108. Concurrently, the other display screen 1001/108 directs the patient to compare the pill in hand with the pill on the display screen to assure it is the same pill. In yet another embodiment, the direction to the patient can be given audibly via speaker 114.

Figure 3:
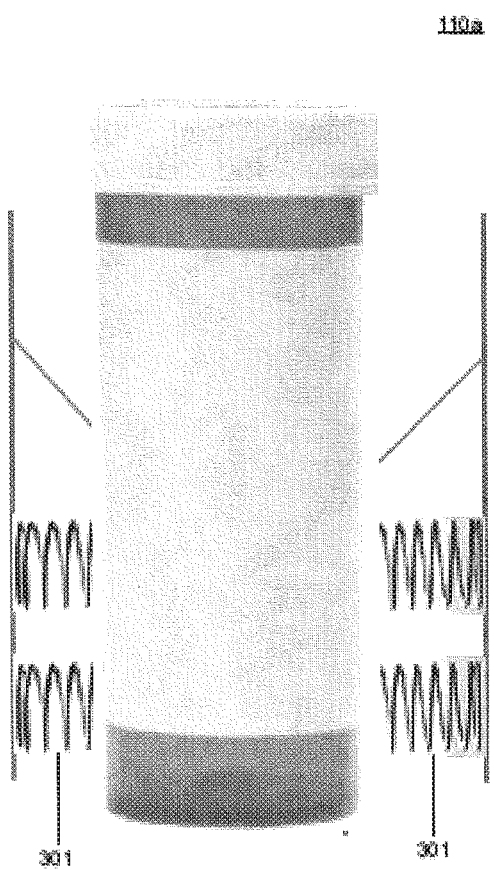
FIG. 3 illustrates a receptacle for original medication containers in an embodiment of the present disclosure.

Receptacles 110 can hold the various original medication containers. Some of the receptacles can be designated as bottle receptacles 110a and dimensioned to receive standard sizes of pill bottles, liquid dropper bottles, and the like. Other receptacles can be designated as non-traditional receptacles 110b, which are capable of receiving, for example, blister packs, or boxes of medication. An individual medication bottle holder receptacle or slot 110a can contain a securing mechanism, such as spring loaded sides 301, as shown, for example, in FIG. 3. These spring loaded sides 301, for example, can apply tension to the original medication container and keep it tightly fitted in the slot 110a and greatly decrease the chances that the original medication container falls out of the slot during movement and/or transport of the home medication manager 100. Other mechanisms for securing the original medication container in the slot can also be used including, but not limited to, a locking clasp that secures the medication (not shown), magnets, or a liner overlaying the innermost surface of slot 110a that securely contacts the outermost surface of the medication bottle, thereby creating friction capable of holding the medication bottle in the slot 110a during transport.

In one embodiment, the home medication manager 100 can be powered by an AC power source 112 or rechargeable battery 202 as shown in FIG. 2. A power supply/charging circuit 204 can be coupled to the AC power source 112 and the battery 202. The power supply/charging circuit 204 can control charging of the rechargeable battery when the home medication manager 100 is plugged into an AC power source 112. Additionally, the power supply/charging circuit 204 can condition the output power from the AC power source 112 or rechargeable battery to provide appropriate voltages and currents to the various components of the home medication manager 100. The home medication manager 100 can accept 12V, 110V, 220V power input, but is not limited to this. Whenever any external power sources are available, the home medication manager 100 can be powered by this available external source and in addition the internal rechargeable battery, such as a Lithium-Ion battery, can charge. If external power is lost, there can be a seamless switch over to the internal battery and when external power is restored there can be a seamless switchover back to the external power and the internal battery can begin charging.

The home medication manager 100 can have a hardware processor or controller 206, such as a microcontroller or Field. Programmable Gate Array (FPGA), which can perform various operations. The controller 206 can execute instructions as described below. These instructions can be stored, for example, on a memory device and/or computer readable medium, such as a computer readable storage device 208. The computer readable media may be any available non-transitory media that is accessible by computer system, and it may include both volatile and non-volatile media, and removable and non-removable media, such as random access memory (RAM) and/or cache memory or others. A hardwire network connection can be provided to the controller to allow for data transfer and/or software upgrades. In addition, or in the alternative, wi-fi can be included to enable the controller to connect with one or more external sources. In one embodiment, the controller can communicate with smartphones and/or tablets, as well as a wrist band and/or pendant 300, a compact electronic box 1401, and/or the removable tote portion (1700a, 1800a, 1900a) of a base 104.

The controller 206 can control scanning of the original medication container by the scanner 106 and can provide instructions and/or alerts through the one or more display screens 108/1001. Additionally, when scanning an original medication container, the controller 206 can determine whether the medication is a new medication or a refill by referencing information stored in the memory/storage device 208. In one embodiment, a database of current managed medications, which is discussed in more detail below, is stored in the memory/storage device 208. New medication can be added to this database or to other data stored in the memory/storage device 208. Additional information regarding the scanned medication, such as usage instructions, number of refills and expiration date can be acquired from, for example, interaction with a pharmacy database, or cloud based network of remote servers ("cloud database") the indicia scanned from the original medication container, if available, or through interaction with the patient/user via the display screen 108. This information can be stored in the database of current managed medications, as well on a pharmacy database, if applicable.

A controller 206 can also select an available receptacle 110 to receive new or refill original medication container(s) and can indicate the selection by illuminating a light (e.g., LEI)) 210, as set forth in FIG. 2, which is associated with the selected receptacle 110. A sensor 212, such as photodiode and LED assembly, disposed inside each of the receptacles 110 can be triggered when the original medication container is received by the selected receptacle 110. Other sensors, as known to one skilled in the art, can also be used. The trigger of the sensor is received by the controller 206 which verifies that the original medication container has been placed in the correct receptacle 110. In certain embodiments the sensors 212 are magnetic sensors, which are triggered by interference with a magnetic field when a medication container is present in the receptacle 110. In yet another embodiment, the sensors 212 are optical sensors, including cameras, light sensors, scanners (e.g., barcode or RFID scanners) or other means for visually detecting when a medication container is present in the receptacle 110. In another embodiment, the sensors 212 are sensitive to the physical mass of a medication container, whereby the sensor is, for example, triggered by direct physical contact (or lack thereof) with a medication container in the receptacle 110. The controller can associate the receptacle assignment, e.g., location, with the medication held in the original medication container and stored in the assigned receptacle, e.g., location, in the database of current managed medications.

The controller 206 may indicate a time for taking a medication by referring to inputted information by the patient/user, or based on information obtained from a pharmacy database, or based on known interactions with other prescribed medications under management. For example, if medication A and medication B should not be taken together, the controller 206 will adjust administration times accordingly. In one embodiment, time can be tracked by a clock circuit 214. Moreover, the controller 206 may adjust the timing of medication administration so that a patient is not alerted to take the medications during preset sleep hours, for example between 11 PM and 8 AM, or other time intervals set by the patient.

When it is time for a medication to be taken, the patient is notified by a notification means such as a buzzer 216, which in certain embodiments may provide a vibrating alert to the user, or short range wireless communication provided by a wireless communication circuit 218, such as Bluetooth, in communication with a portable electronic device including, for example, a paired bracelet, e.g., wrist alert, or fob, which can be worn, for example, as a pendant 300, a cell phone, smart phone, tablet or software application thereof, or any other Bluetooth or wi-fi compatible device know to one of ordinary skill in the art. In one specific embodiment, the notification can occur when the bracelet or pendant 300 lights up and/or vibrates. In a specific embodiment, the notification to take a medication occurs when the home medication management system communicates through wi-fi or Bluetooth to a cell phone, tablet or smart phone, causing the cell phone or smart phone to ring and/or vibrate. Other notification means can also be used. Additionally, the controller 206 can activate the LED 210 corresponding to the receptacle 110 holding the medication to be taken. If the patient inadvertently retrieves a medication from the incorrect receptacle 110, the controller 206 can detect the occurrence by way of the sensor 212 associated with improper receptacle 100 and can display a warning message on the display screen 108 and/or can sound an alert by way of the buzzer 216 and/or the speaker 114. In one embodiment, the controller 206 can modulate (e.g., raise) the height of the appropriate medication container in the corresponding receptacle 110 holding the medication to be taken by. Modulating the height of an appropriate medication container within a receptacle 110 can be achieved by any mechanical means for raising and lowering items, as known to one skilled in the art.

In the case where the medication must be refrigerated, and thus not held in one of the receptacles 110, the controller 206 can provide instructions on the display screen 108 to retrieve the medication from the refrigerator and can scan the barcode of the original medication container prior to administration. Scanning the barcode of the refrigerated original medication container prior to administration allows the controller 206 to verify that the correct medication is being taken.

Retrieval of the correct medication from the indicated receptacle 110 can be detected by the controller 206 by way of the sensor 212, as well. The controller 206 can record the time and date of the dosing in a database stored in the memory; storage device 208. This database can be the same as the database of current managed medications or can be a separate database, such as a pharmacy database. In one embodiment, the data can be stored on an external device, such as a server, cloud database, and/or portable electronic device (e.g., cell phone, tablet and/or smartphone). In another embodiment, the data can be stored in an RFID chip 500.

The controller 206 may provide further instructions, such as instructing the patient to take a certain number of pills or amount of liquid medication, to take the medication with food, or refrain from eating for a period after taking the medication. The instructions can be provided via the speaker 114, and/or a display screen 108, and/or a wrist alert, or fob, which can be worn, for example, as a pendant 300, a cell phone, smartphone, tablet or software application thereof.

The wireless circuit 218 can include multiple communication protocols, such as Bluetooth, 802.11a/b/g/n, and CDMA, GSM and 3G/4G/4G LTE mobile phone communication protocols. 802.11a/b/g/n and mobile phone communication protocols can be utilized by the controller 206 to contact a medication database service (e.g., pharmacy database or cloud database) for retrieving medication information relating to drug interactions, administering information, etc. In one embodiment, a cable, such as network cable with a RJ45 connector 116, can be used to communicate to devices external from the home medication manager 100. The wireless circuit 218 and/or the cable can allow the controller 206 to contact a treating health organization to relay medication compliance information and other related information for the patient's health records. The controller 206 can be configured to provide encryption and decryption when sending or receiving personal health-related information in order to maintain patient privacy; in one embodiment the data will be HIPAA (Health Insurance Portability and Accountability Act) compatible. In one embodiment, the controller 206 can allow sharing of data regarding compliance, errors, device malfunction; in addition, the controller can perform updates and changes to the current therapy. In a specific embodiment, the controller shares stored data related to the amount of a particular medication being managed by the home medication device with a pharmacy database or other external database (e.g., cloud database).

As mentioned above, the home medication manager 100 can have one or more databases in the memory/storage device 208. In one embodiment, one database includes only data from current medication management, such as data obtained when scanning the original medication container, such as name of medication, name of manufacturer of medication, image of the medication, dosage instructions, administration instructions, e.g, frequency, administration time, storage instructions, expiration date, remaining refills, interaction data, special instructions, etc., and data indicating in which receptacle the original medication container resides, and one or more additional databases comprising information regarding patient data for the user of the home medication manager, data regarding medication interactions, compliance information, etc. In one embodiment, one database comprises all of the data and information for the patient, the medications, compliance, prescribing doctor, pharmacist, etc.

Figure 4:
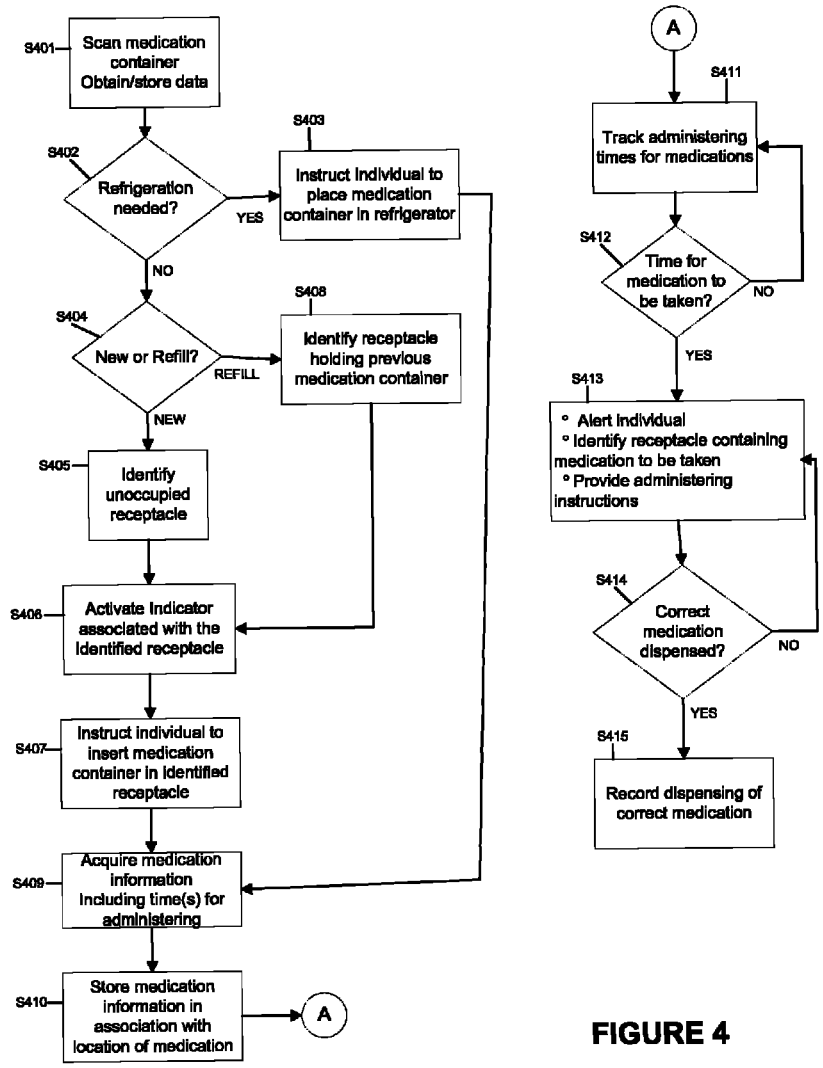
FIG. 4 is a flow diagram of a process executed by an embodiment of the present disclosure.

FIG. 4 is a flow diagram of the inventive method. In step S401, an original medication container is scanned to obtain indicia or usage medication related information, such as medication name, manufacturer's name, dosage instructions, administering times, expiration date, remaining refills, storage instructions, interaction information, etc. In one embodiment, the medication is accepted into the system via a barcode placed on the medication container by the pharmacist. In step S402, a determination is made, based on the obtained storage information, whether or not the medication needs refrigeration. If refrigeration is needed (S402=YES), then at S403 an instruction is given to place the medication container in the refrigerator, and processing continues at S409.

If refrigeration is not needed (S402=NO), then at step S404, a determination is made as to whether or not the medication is new or is a refill. If the medication is new (S404=NEW), then at step S405, an unoccupied receptacle, e.g., location, is identified. At step S406, an indicator associated with the identified receptacle is activated. For example, in one embodiment, the receptacle is lit to indicate the identified, activated receptacle. At step S407, an instruction is issued to the user to insert the original medication container into the identified receptacle. This instruction could be, for example, displayed on the display screen and/or issued through the speaker. The process continues at S409.

If the medication is a refill (S404=REFILL), then at S408, the receptacle holding the previous medication container is identified. This identification could be done by lighting up the receptacle, by displaying a message on the display screen, by issuing a message using the speaker, by a wrist or fob alert message, or any combination thereof.

At S409, the updated medication information can be acquired from an external database (e.g., pharmacy database or cloud) via wireless circuit 218. For example, when a new medication is prescribed information is acquired and added to the database remotely. In another example, when a change in the frequency or dosage of a medication is made, such information can be acquired and updated in a database. At S410, the medication information associated with the location of the medication is stored. At S411, administering times are tracked. At S412, whether or not it is time for a medication to be taken is determined. If it is time (S412=YES), an alert is issued at S413, the receptacle containing the medication to be taken is indicated and instructions for taking the medication are provided. The receptacle can be indicated by lighting up the receptacle, by displaying a message on the display screen, by issuing a message using the speaker, by a wrist or fob alert message, or any combination thereof.

At S414, whether or not the correct medication has been dispensed is verified. For example, an image of the proper medication will be displayed on display screen 108 for comparison the medication removed by the user. If the medication displayed by the home medication manager (100) matches the medication removed by the user, (S414=YES), dispensing of the correct medication is recorded and the tracking can resume at S411.

If it is not determined that the correct medication has been dispensed (S414=NO), the process returns to step S413.

If it is not time (S412=NO), tracking continues at S411.

One embodiment of the home medication manager 100 can be an apparatus about the size of a shoe box, can weigh less than two pounds and can have a lock down top with a carry handle and a rechargeable battery system. In one embodiment, the present invention has a display screen and voice over IP that reminds the individual what to take, e.g., food and/or water, or not take, with his or her medication. This reminder information can be retrieved from an internal or external database. When the medication is not stored in the inventive apparatus, for example because the medication has to be refrigerated, display screen 108 can provide the instruction "YOUR MEDICATION IS IN THE REFRIGERATOR" and display an image of the medication for guidance.

Additionally, individuals being monitored by a home health agency that belongs to a Regional Health Information Organization/Health Information Exchange system can have their medication information and medication compliance added to the individual's Electronic Health Record and/or sent to the health care provider, pharmacy, and/or the emergency room by way of a wireless, internet, or mobile communication. The wireless technology in the home medication manager can remove many of the potential errors that are associated with self medicating, and offers family members, home health agencies, primary care physicians, pharmacists, etc., access a patient's compliance. The system can also alert a pharmacy when the medication needs to be refilled.

Figure 5:
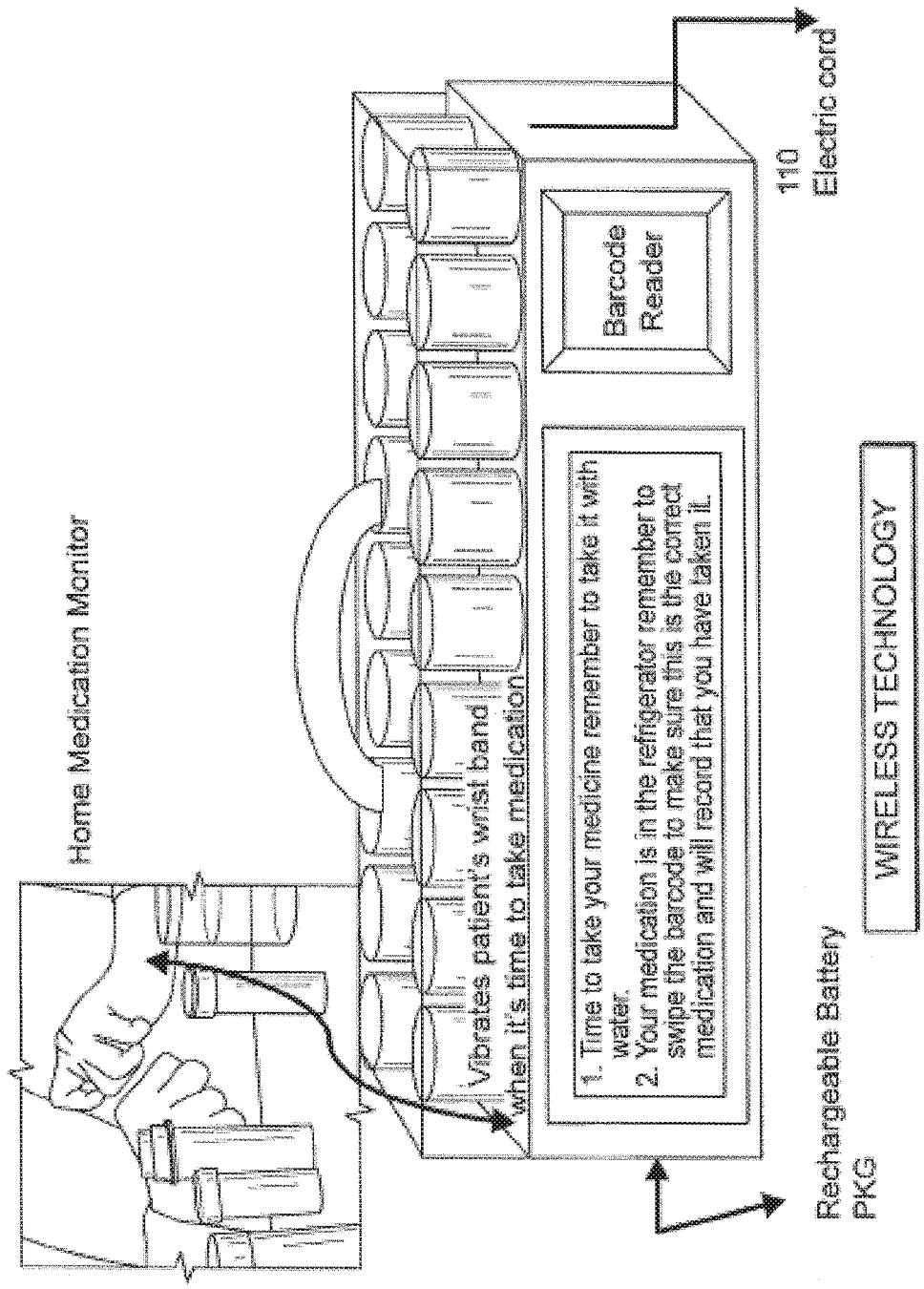

FIGS. 5-8 illustrate aspects of embodiments of the present invention. FIG. 5 illustrates the power sources of the rechargeable battery and the electric cord, as well as wireless technology which can be used to communicate with a wrist alert, or fob, which can be worn, for example, as a pendant 300, a cell phone, tablet, smartphone or software application thereof.

Figure 6:
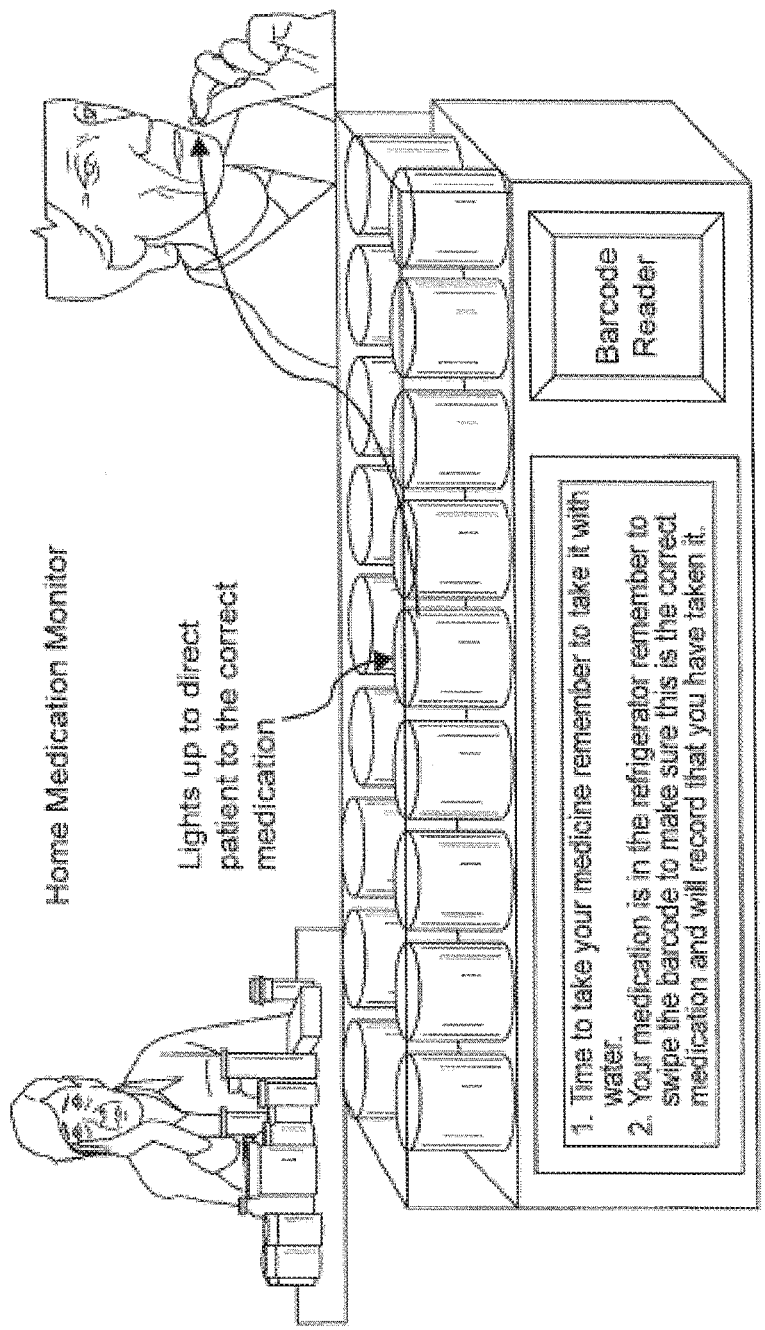

FIG. 6 illustrates indicating a receptacle, e.g., lighting up and/or vibrating the receptacle, to direct the user/patient to the correct medication container. As shown in the embodiment of FIG. 6, the user is notified to administer a medication by illuminating and/or vibrating a receptacle and displaying instructions on the display screen 108, which may include an image of the medication contained within the indicated receptacle. In the embodiment shown in FIG. 6, the message reminds the patient that it is time to take your medicine, reminds the patient to take the medication with water, the location of the medication (i.e., to get the medication from the refrigerator where it is stored) and/or to swipe the original medication container barcode to make sure the correct medication is being taken. The home medication management system can record that the patient has taken, e.g., swiped, the correct medication and store or transmit such information to a database.

Figure 7:
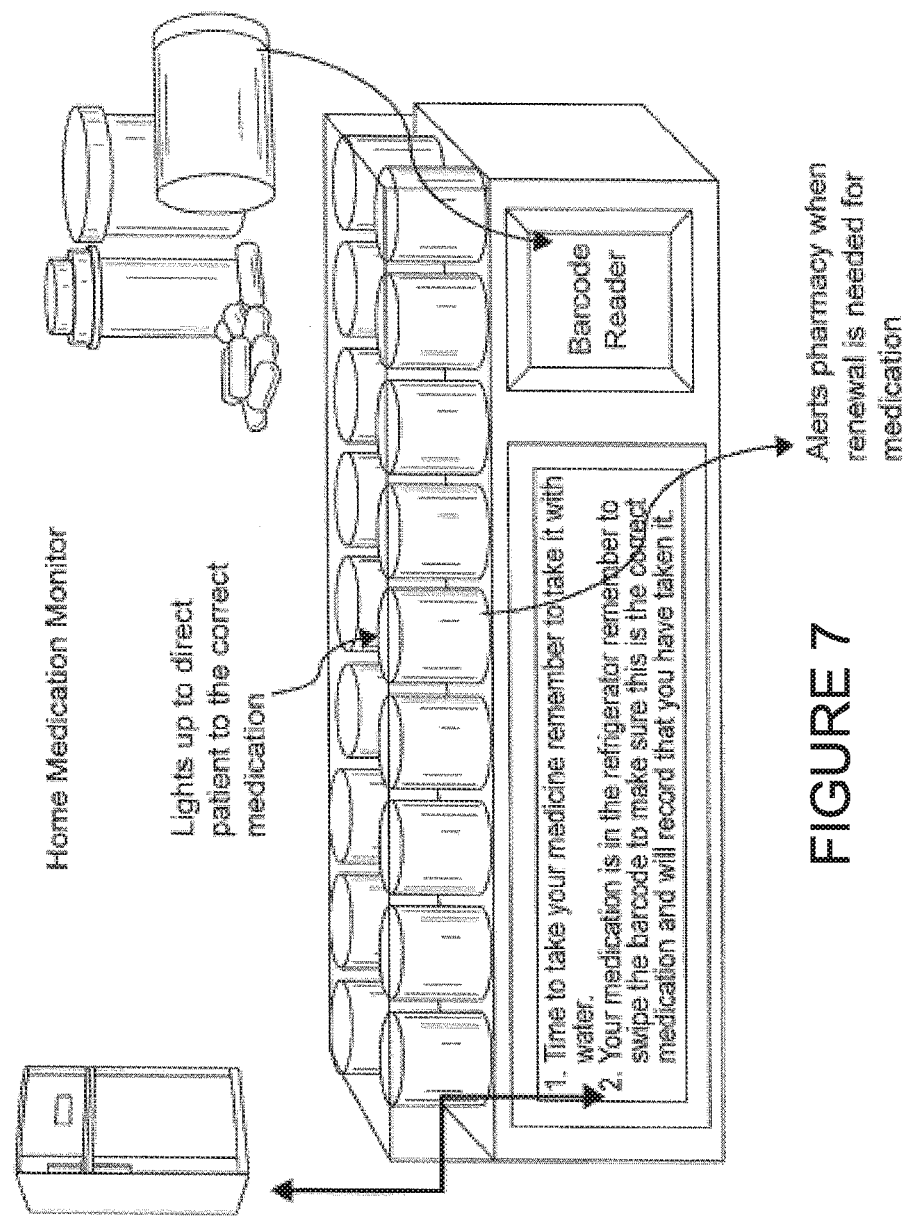

FIG. 7 illustrates that the pharmacy can be alerted when renewal for a medication is needed or coming due (i.e., 10 to 30 pills remaining in a 1 month or 3 month supply of medication). In the embodiment shown in FIG. 7, the wireless circuit 218 and/or the cable of the home medication manager can allow the controller 206 to contact a treating health organization or pharmacy to relay medication compliance information and other related information for the patient's health records and/or to alert a patient's health care provider or pharmacist that renewal for a medication is coming due.

FIG. 8 illustrates a lockable carry cover for one embodiment of the invention, both attached to the base (top) and detached from the base (bottom).

Figure 9:
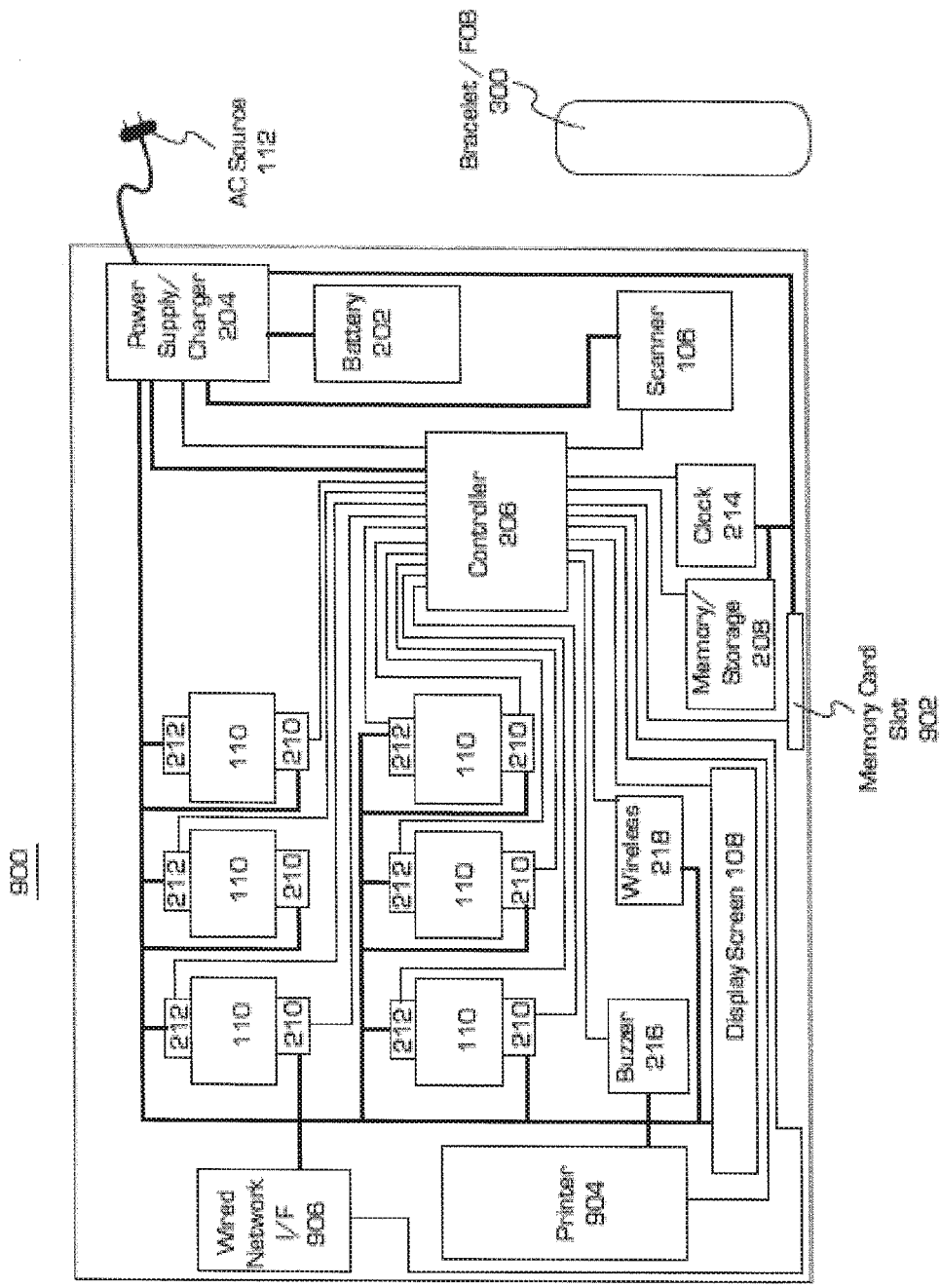
FIG. 9 illustrates a block representation of an embodiment of the present disclosure.

In another embodiment, as shown in FIG. 9, the home medication manager 900 includes all the elements described with respect to FIG. 2 above. Elements of the present embodiment that correspond to like elements in the embodiment of FIG. 2 are assigned like reference numerals in FIG. 9. In addition to the features of the embodiment of FIG. 2, the present embodiment further includes a memory card slot 902 configured to read from and write to a standard memory card, such as multimedia cards (MMC), secure digital (SD) cards—including SD high capacity (SDHC) and SD extended Capacity (SDXC) cards, memory stick, Compact-Flash, Smart Media, and xD cards. Alternatively, the memory card slot 902 can be replaced with a universal serial bus (USB) connector capable of reading from and writing to a flash memory drive, commonly referred to as a flash thumb drive.

The memory card slot 902 allows removable storage on a memory card (not shown) of a patient's medical information relating to the administration of prescribed medication. For example, the memory card inserted into the memory card slot 902 may contain a list of prescribed medications provided by a pharmacist, which includes dosages, amount of medication provided in a particular prescription (e.g., 1 to 2 week supply, 1 month supply or 30 pills, 3 month supply or 90 pills, etc.) and frequency of administration that is entered by a pharmacist or other medical professional, or written to a removable storage component via an external database using wireless circuit 218 and/or the cable of the home medication manager and controller 206. This allows the medication information to be entered into the home medication manager 900 of the present embodiment more efficiently by not requiring manual entry of the information by the patient. In certain embodiments, memory card slot 902 enables a user to write and/or store patient data relating to a patient's prescribed medications, which can then be transported and provided to a pharmacist or health care provider by removing the removable media (e.g., SD card or USB) from memory card slot 902.

In one embodiment, the memory card can allow for software upgrades, and can allow data to be imported into various Apple-Based®, Linux-based, and/or Windows®-based programs to improve monitoring of patient care.

The home medication manager 900 also includes a printer 904 disposed within the housing of the home medication manager 900. The printer 904 can be configured to provide a hardcopy report of a patient's medication usage and or prescription compliance. In addition, the printer 904 may be configured to allow a medical professional to provide written instructions to the patient by way of either the wireless circuit 218 or a wired network interface 906 using any of the protocols defined under the IEEE 802.x family of standards. Such written instructions may include changes to administering instructions as well as a new prescription to be presented to a pharmacist for fulfillment. In one embodiment, the printer 904 can print out one or more preformatted reports such as medication compliance, histograms, doctor visit summary, time to reorder notice, amount of medication remaining in a prescription, etc.

The wired network interface 906 allows connection of the home medication manager 900 to connect to a local area network (LAN) and/or a wide area network (WAN), such as the Internet, or through the Internet using an Internet Service Provider, for example. In one embodiment, communication with smartphones and/or tablets can be enabled. In a specific embodiment, a wired network interface 906 connects the home medication manager to a LAN by way of the controller 206, which enables communication between the home medication manager 900 and a smartphone, tablet and or database. In another embodiment, wireless circuit 218 communicates (e.g., connects to a wi-fi signal or wireless network), which enables communication between the home medication manager 900 and a smartphone, tablet and or database (e.g., pharmacy or health care provider network).

Figure 13:
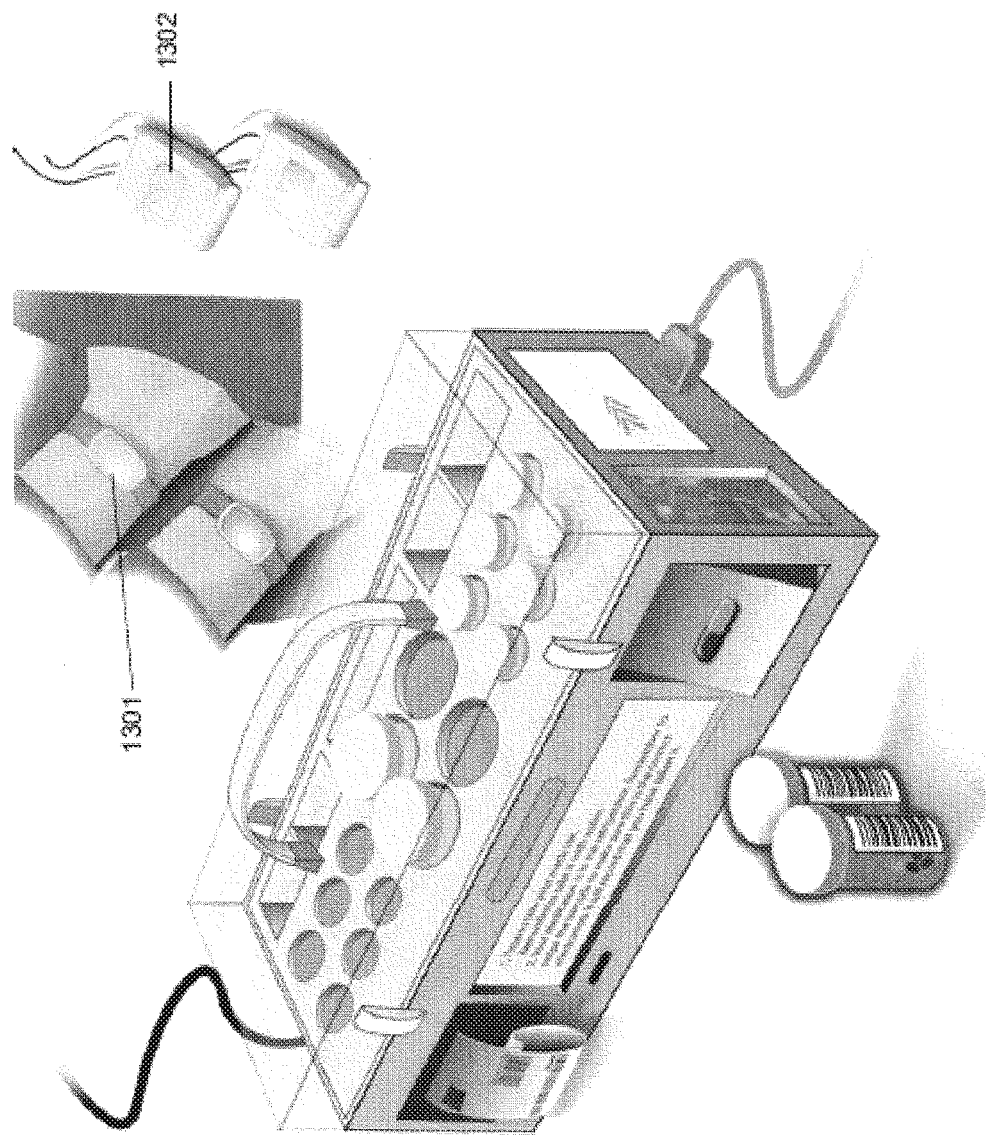

In one embodiment, the home medication manager will contain both a speaker and a microphone 114 for the purpose of communicating with the user via voice recognition software. These devices can be located in the base housing, for example, just above the main LCD screen. The speaker can duplicate in voice what the screen is displaying. This will give the patient two ways of receiving instructions. Third party voice recognition software can be used. For example, when it is time to take the medication, the home medication manager can remind the patient (via the vibrating and or a blinking light on the wrist band 1301 and/or on the pendant 1302, and/or a voice prompt) as shown, for example, in FIG. 13, to go to the medication manager. Upon arrival at the medication manager, the patient sees that a particular receptacle or holder is indicated; this receptacle holds the original medication container, or bottle, containing the medication the patient is reminded to take. If the patient removes the wrong bottle, an alert tells the patient that the wrong medication is being removed.

Figure 12:
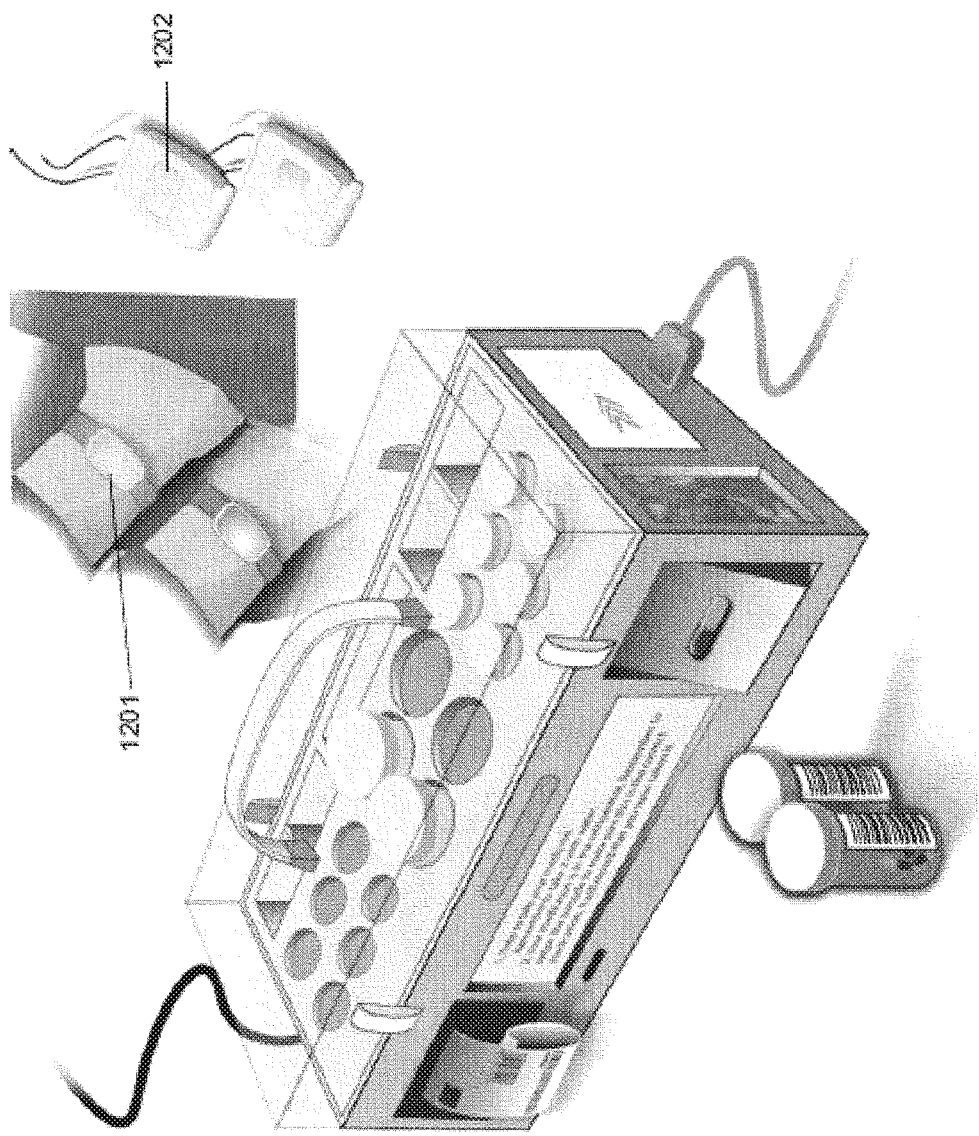

In one embodiment, the present invention accepts the medication into the system via a barcode placed on the medication bottle by the pharmacist. When scanned by the barcode reader, the home medication manager directs the patient, for example, by voice over IP and screen display, to place the medication bottle in the illuminated slot 1201, as shown in FIG. 12. This can he followed by the system naming the medication, describing the dosage and stating when to take the medication. This can be followed by voice over. IP and a screen display message; "You need to take this medication once in the morning and once in the evening. What time would you like to take this medication in the morning?" User responds "7 AM" using microphone/speaker element 114. The home medication management system then responds by confirming, "you said 7 AM, is this correct?" User responds "YES", and this information can be saved or stored by the home medication manager system via database or stored in the memory/storage device 208. The home medication manager then responds "what time would you like to take your medication in the evening?" User responds "6 PM". The home medication manager responds "6 PM, is this correct?" User then responds "YES" using microphone/speaker element 114, and this information is saved in the system via database or stored in the memory/storage device 208.

Figure 14:
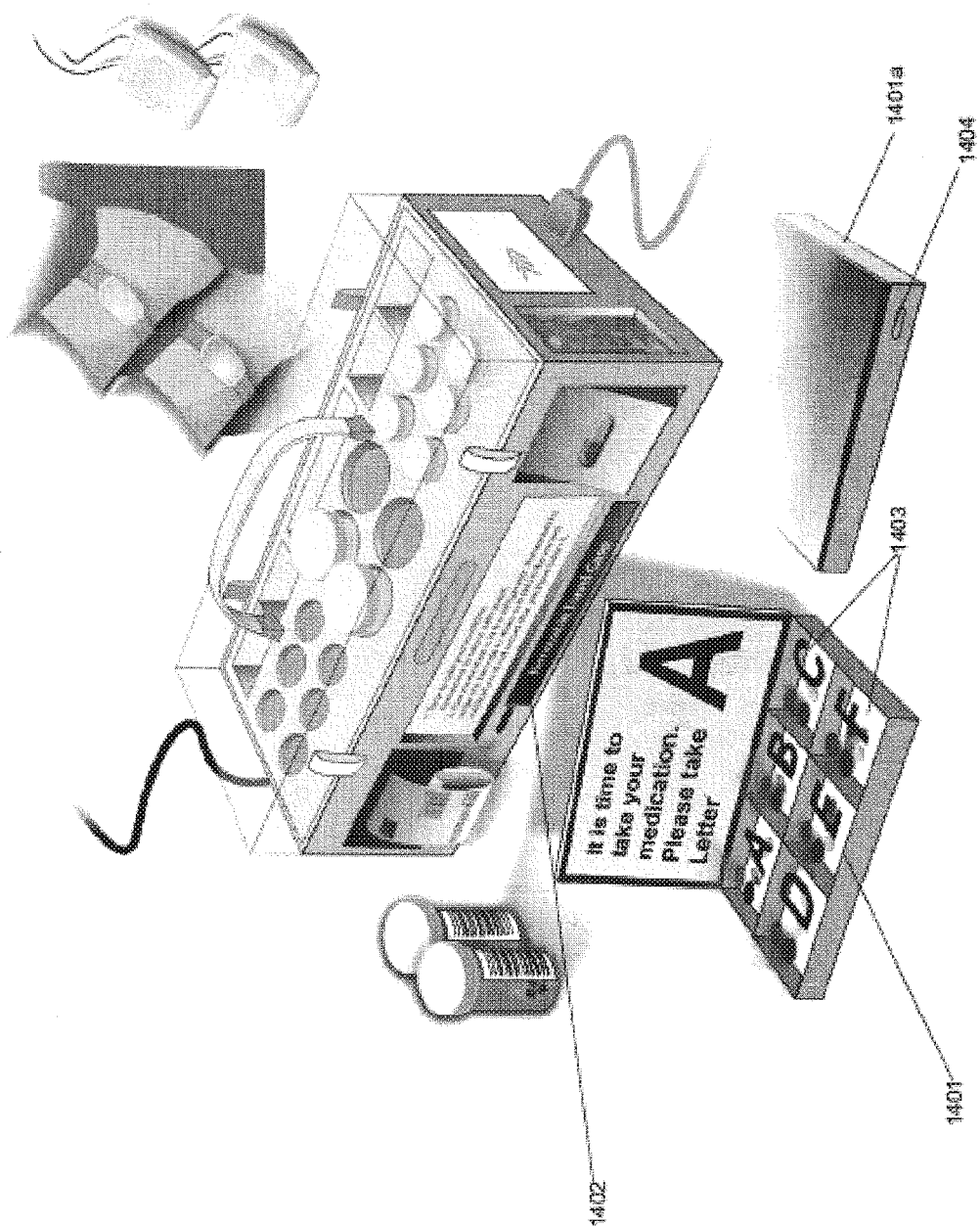
FIG. 14 illustrates a specific embodiment of the home medication manager containing a compact electronic box component.
Figure 15:
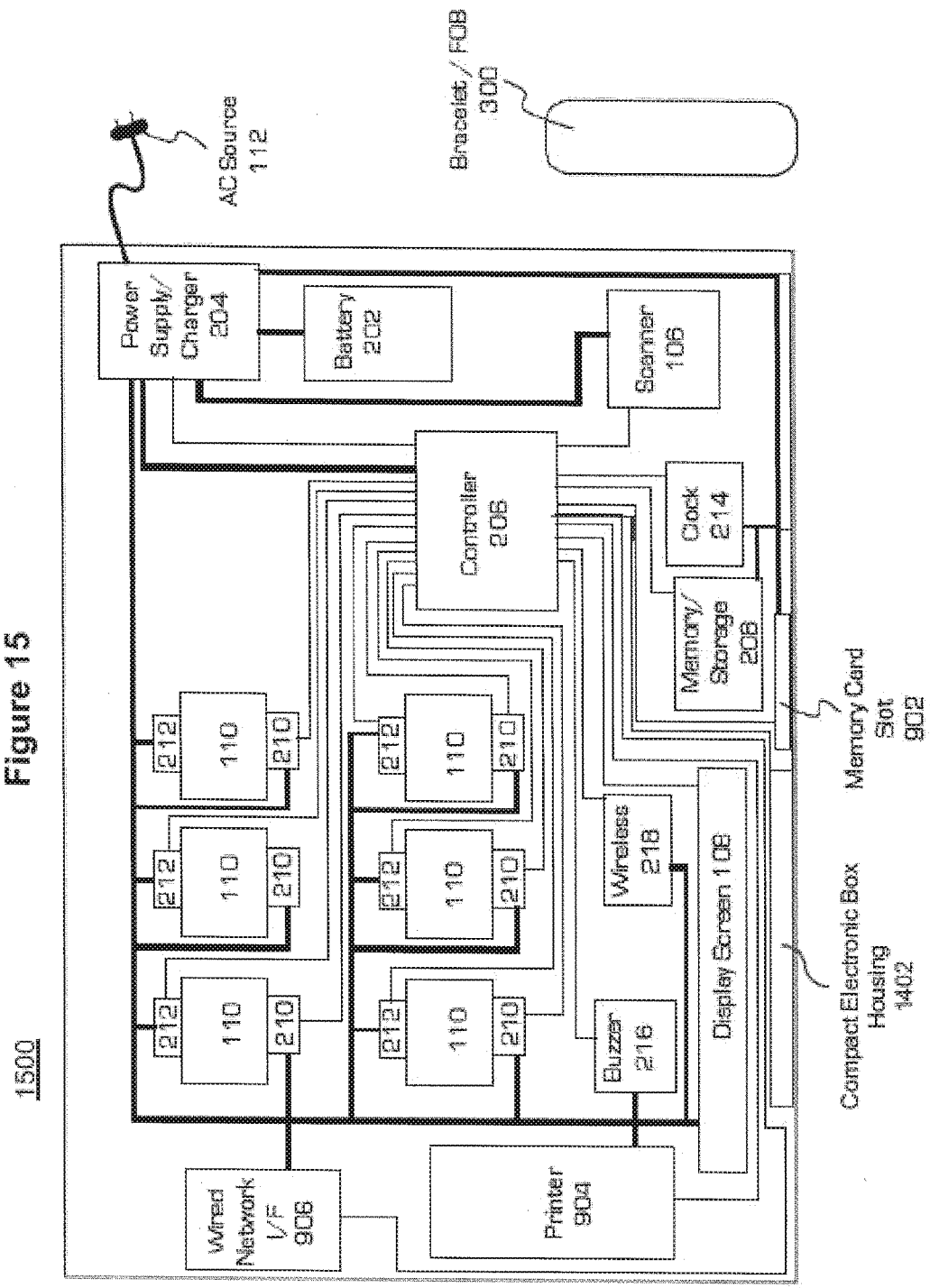
FIGS. 15-16 illustrate block representations of certain embodiments of the present disclosure, which include the compact electronic box element.

In one aspect of the instant disclosure, the medication management system integrates a smaller, compact electronic box 1401/1401a, which enables an individual to take medication remotely (i.e., away from the home or home medication manager) without taking the home medication management system 100/900, for up to 6 doses over a 24 hour period, as shown in FIG. 14. FIG. 15 shows one embodiment of the instant disclosure whereby a compact electronic box 1401a is housed within compartment 1402 of the home medication manager 1500. When compact electronic box 1401a is housed within compartment 1402 of the home medication manager system 1500 the compact electronic box will securely lock into place via locking element 1404, as shown in FIG. 15. To release the compact electronic box 1401a from the home medication manager system the user need only to depress locking element 1404, which will enable the user to easily remove the compact electronic box from within compartment 1402.

Figure 16:
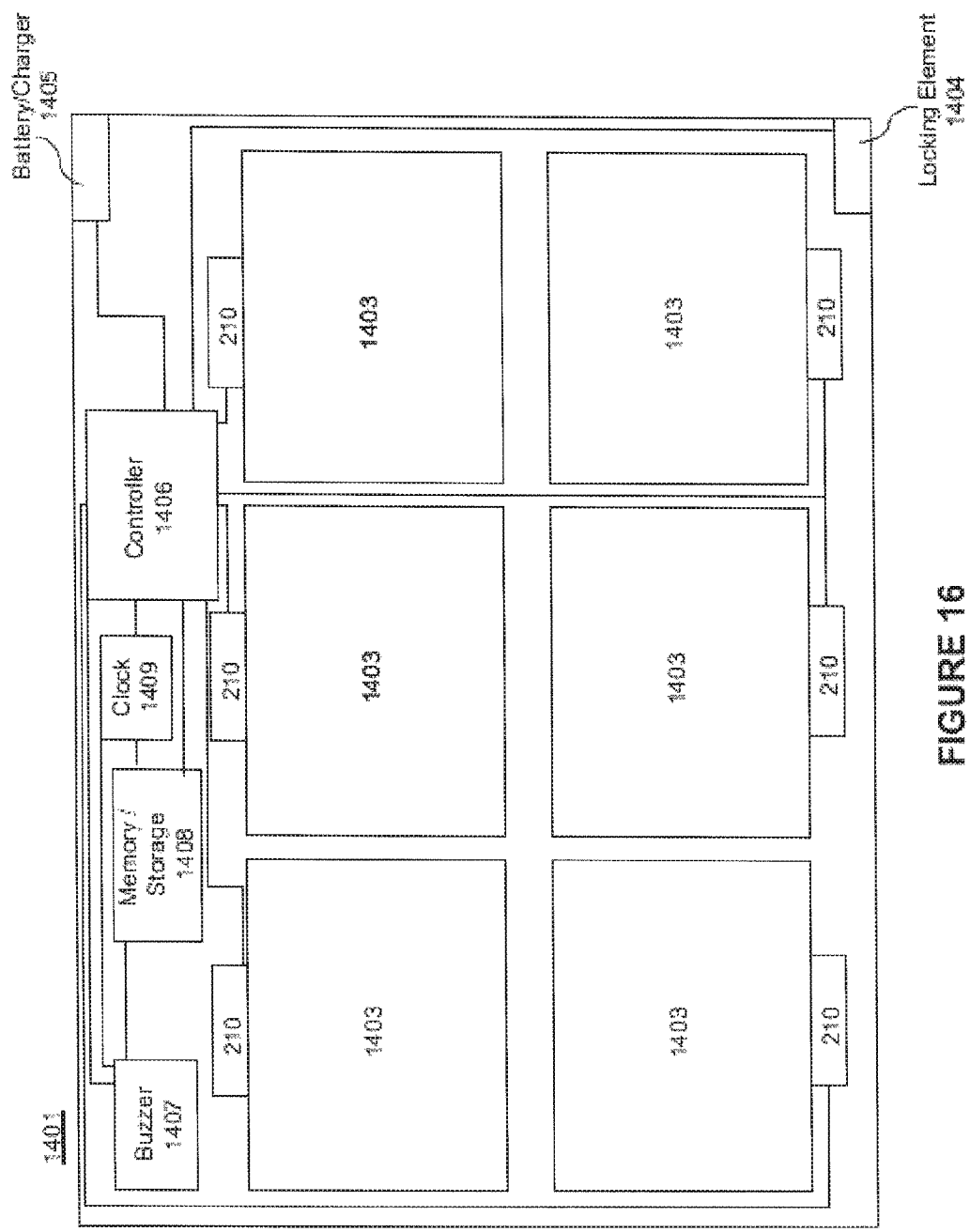

In one embodiment of the instant disclosure, when compact electronic box 1401a is housed within compartment 1402 it is coupled to the home medication management via a connection (not shown) that enables communication with the home medication manager's controller 206, memory/storage component 208, clock 214 and power supply/charger 204, as shown in FIG. 15. While in compartment 1402, a battery/charger element 1405 located within compact electronic box 1401 is charged through its connection to power supply/charger 204 of the home medication management system 1500. In certain embodiments, when compact electronic box 1401a is housed within compartment 1402 it is connected to controller 206, which can execute instructions as described below or communicate stored instructions, i.e., instructions stored on a memory device and/or computer readable medium 902 or computer readable storage device 208 of the home medication manager 1500, to a controller 1406 located on compact electronic box 1401, as shown in FIG. 16. Further in a specific embodiment, the compact electronic box 1401 contains a clock 1409, memory/storage device 1408 and a buzzer 1407, which are connected to a controller element 1406, and can be used to store and/or transmit information between the home medication manager 1500 and the compact electronic box 1401, as shown in FIG. 16. In addition, in certain embodiments, a hardwire or wi-fi network connection can be provided to controller 1406 to allow for data transfer (e.g, from an external database) and/or software upgrades on the compact electronic box 1401 (not shown).

In certain embodiments, compact electronic box 1401 has (four) 4 compartments labeled A, B, C, D, which permits a user to take their medication at 4 different times during a 24 hour period. In this embodiment, if an individual wants to be out for the day or part of the day, he/she goes to the home medication management system 1500 and enters the number of hours he/she will be away from home (e.g., 1-24) using display screen 108. The home medication manager will then process the information provided by the user and identify medications, which are stored within the home medication management system and then illuminate those medications that will need to be taken during the time in which the user is away from home. For example, the home medication manager can direct the individual to put particular medications in compartment "A" and set the "A" tinier alarm to the given time, e.g., the initial time of the "A" time period. All of the medications for compartment "A" will illuminate and, after the medications are removed from their respective containers and the last of the previously illuminated containers placed back in the home medication management system, the lights will shut off. This process is repeated for compartments "B", "C" and "D". Once medications are loaded by the user into compartments 1403 of compact electronic box 1401a the time alarms are set for compartments A, B, C and D, and the user can go out.

In certain embodiments, compact electronic box 1401 has (six) 6 compartments labeled A, B, C, D, E and F which permits a user to take their medication at 6 different times during a 24 hour period. In this embodiment, if an individual wants to be out for the day or part of the day, he/she goes to the home medication management system 1500 and enters the number of hours he/she will be away from home (e.g., 1-24) using display screen 108. The home medication manager will then process the information provided by the user and identify medications, which are stored within the home medication management system and then illuminate those medications that will need to be taken during the time in which the user is away from home. For example, the home medication manager can direct the individual to put particular medications in compartment "A" and set the "A" timer alarm to the given time, e.g., the initial time of the "A" time period. All of the medications for compartment "A" will be lit and, after the medications are removed from their respective containers and the last of the previously illuminated containers placed back in the home medication management system, the lights will shut off. This process is repeated for compartments "B", "C", "D", "E" and "F", if necessary. Once medications are loaded by the user into compartments 1403 of compact electronic box 1401a the time alarms are set for the necessary compartments 1403, and the user can go out.

In yet another embodiment, when an individual wants to be out for the day or part of the day, he/she goes to the home medication management system 1500 and using speaker/microphone element 114 says "On the Go". The home medication manager will then prompt the user to recite the number of hours he/she will be away from home (e.g., 1-24) using voice over IP and speaker/microphone element 114. The home medication manager will then process the information provided by the user and identify medications, which are stored within the home medication management system and then Illuminate those medications that will need to be taken during the time in which the user is away from home. For example, the home medication manager can direct the individual to put particular medications in compartment "A" and set the "A" timer alarm to the given time, e.g., the initial time of the "A" time period. All of the medications for compartment "A" will be lit and; after the medications are removed from their respective containers and the last of the previously illuminated containers placed back in the home medication management system, the lights will shut off. This process is repeated for compartments "B", "C" and "D", if necessary. Once medications are loaded by the user into necessary compartments 1403 of compact electronic box 1401a the time alarms are set for the necessary compartments (e.g.) A, B, C and D, and the home medication management system will inform the user via voice over IP that the user can go out.

When it is time to take the medications stored in the compact electronic box, the user is notified via illumination of an LED or series of LED 210 and/or vibration of a buzzer element 1407 of the compact electronic box 1401, and/or via the wrist band and/or pendant 300. When the individual opens the compact electronic box 1401, the individual compartment 1403 will be illuminated by the corresponding LED 210 indicator, which notifies to the user that the medication located in the illuminated compartment should be consumed. The process repeats until all time periods have passed or the medications in each compartment 1403 have been consumed.

In one embodiment, when the correct original medication container is removed, the patient is requested either verbally or on the display screen, or both, to compare the medication in hand with the picture on the screen 1001, as shown in FIG. 10, to verify that this is the correct pill. After a predetermined time, e.g., one to three minutes, the patient can be asked to put the original medication container back in the indicated receptacle. If patient places the container in the incorrect receptacle, a verbal and/or visual notice can be generated by the home medication manager, saying the container has been placed in the wrong receptacle, and requesting that the container be placed in the indicated holder. In one embodiment, indication of the correct receptacle is provided by illuminating the proper receptacle 110.

In one embodiment, the home medication manager can be portable as it has a lock down cover with a handle and rechargeable battery. This portability allows an individual who is travelling to use the home medication management system without losing the information stored therein. In one embodiment, the unit can include a 12V transformer, a 12V battery, 120V AC and 240V AC. In one embodiment, a fully charged Lithium Ion battery 202 will provide power to the home medication management system for one week.

In one embodiment, the home medication management system can contain a thermal printer 904 in the base housing, as shown in FIG. 9. This printer can be programmed to generate specific reports just by pressing a button. For example, when a patient has a doctor's appointment, he can press a button on the base housing and the printer will print out all the medication the patient is currently taking, the dosage, the frequency and whether the patient has been compliant. The printer can also provide information to the patient, serving as an interface between the patient and the home medication manager, instead of, or in addition to, a voice recognition interface.

Figure 17:
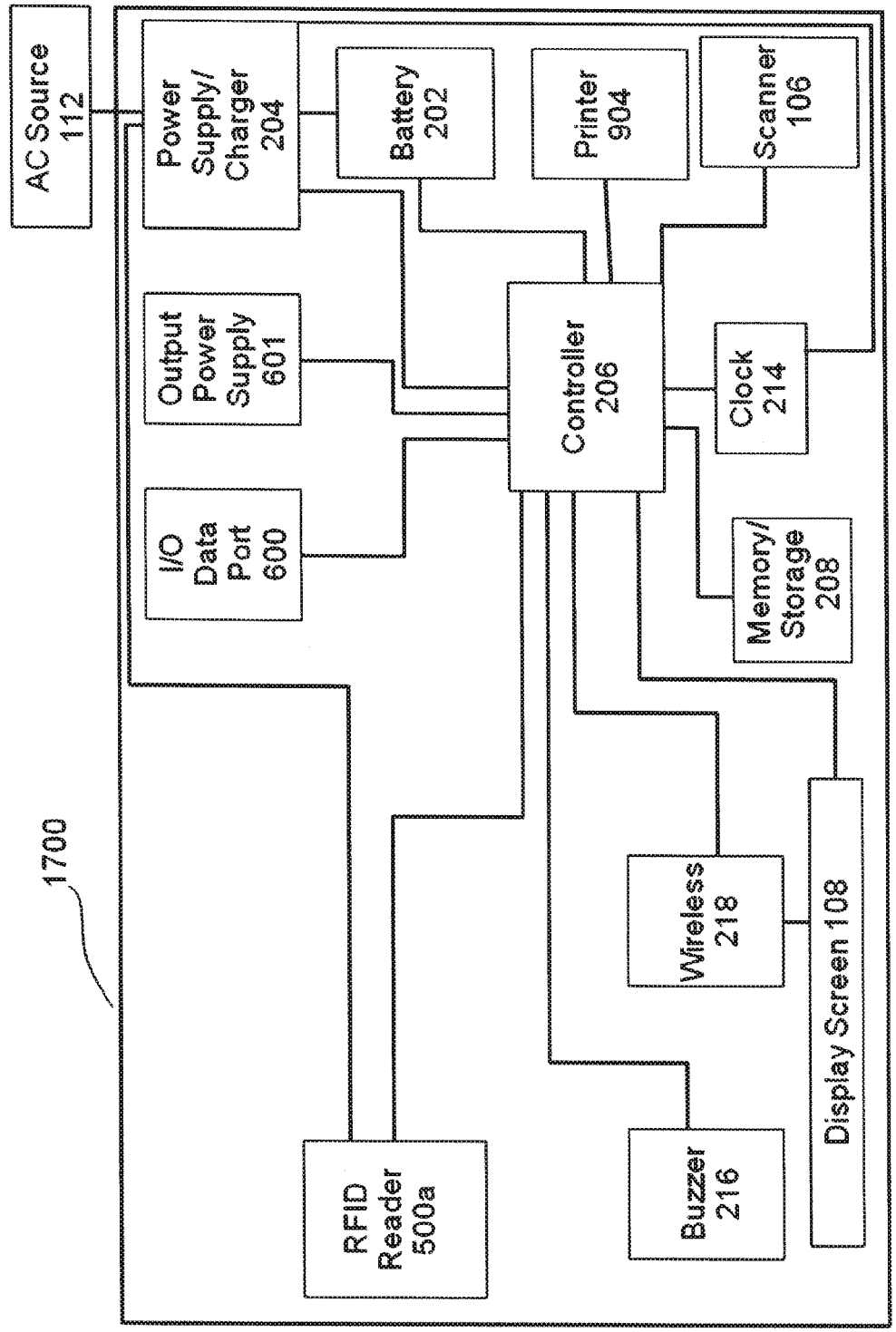
FIGS. 17-18 illustrate block representations of an embodiment of the present disclosure including a base unit having a removable tote element and a docking station.
Figure 18:
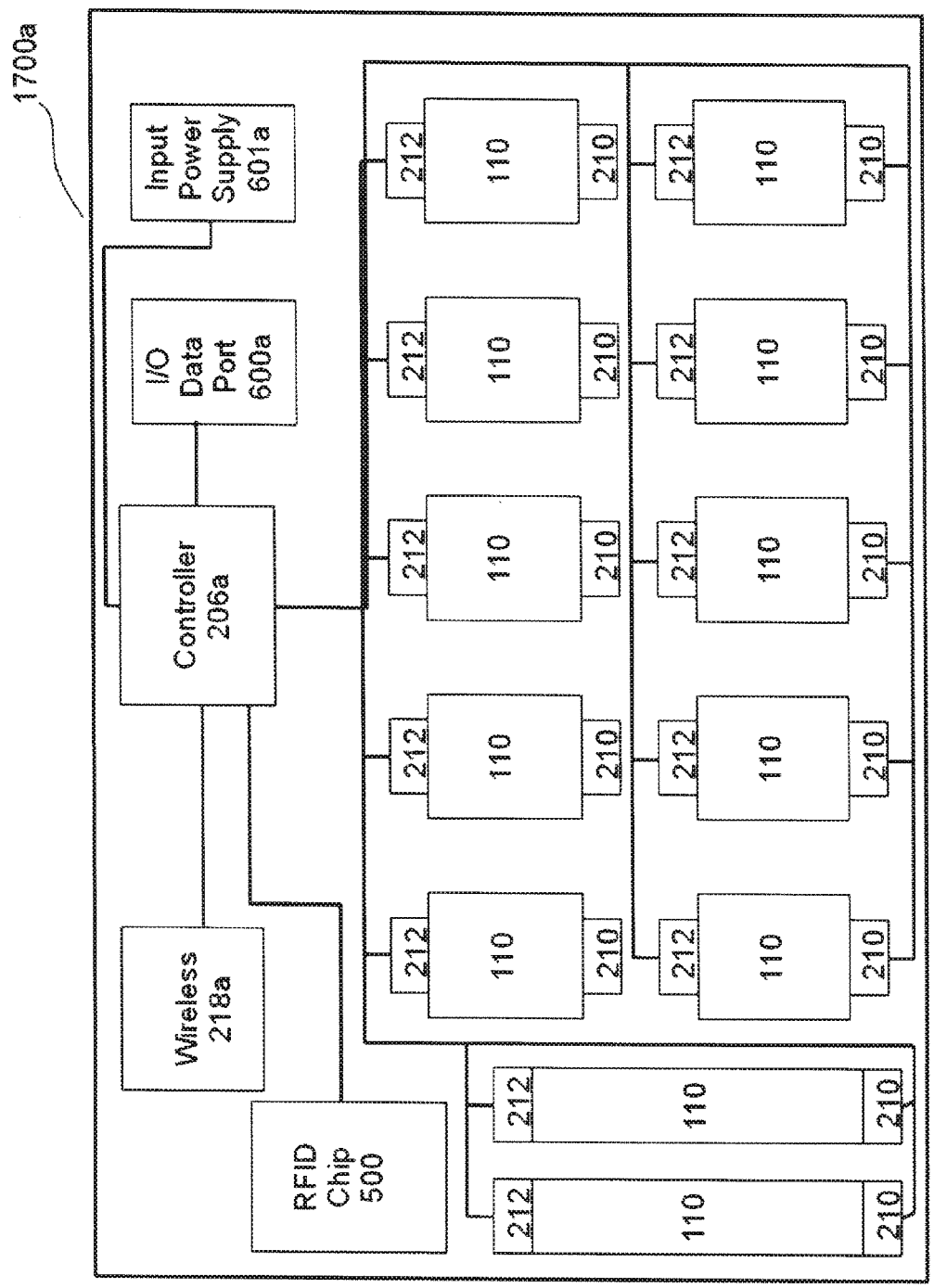
Figure 19:
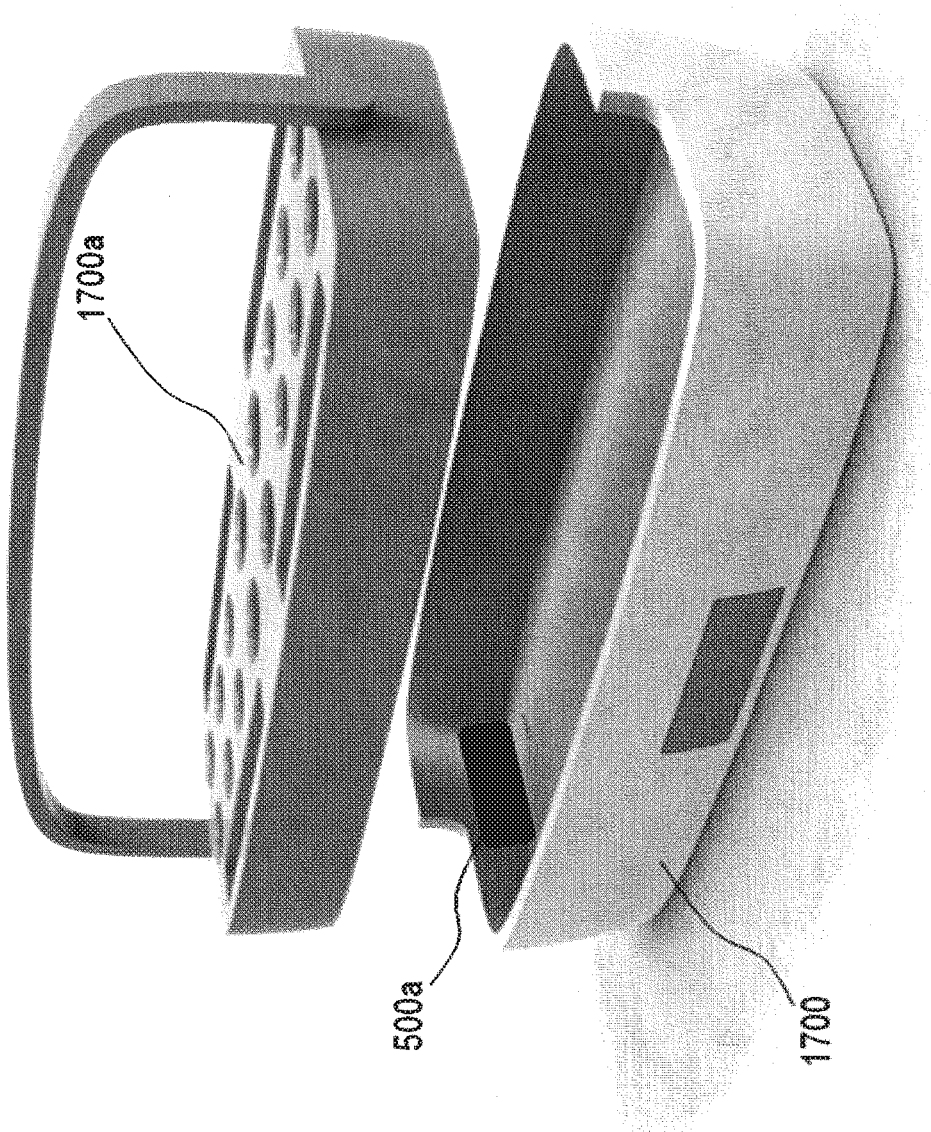
FIGS. 19-20 illustrate a specific embodiment of the home medication manager containing a base unit having a removable tote element and a docking station.
Figure 20:
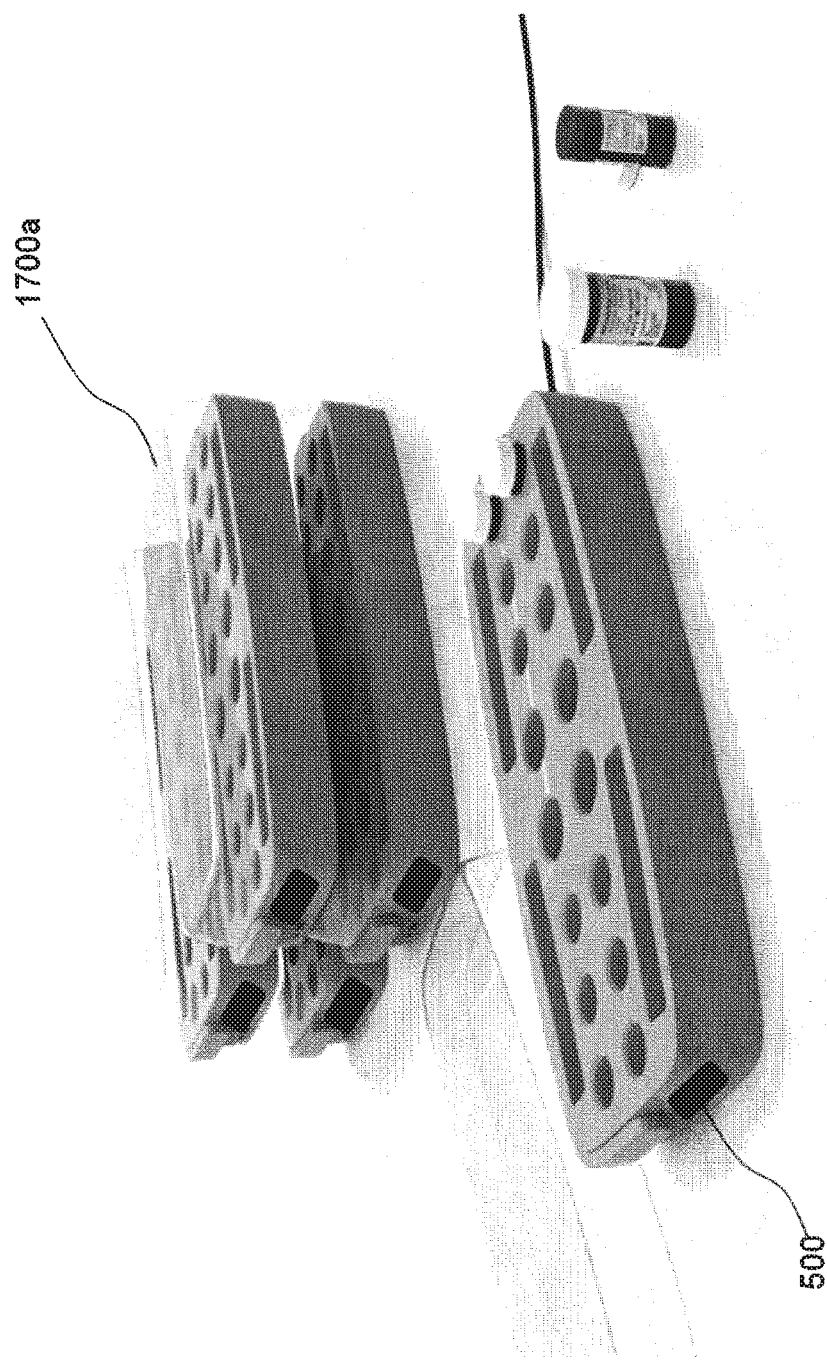

Another aspect of the present disclosure is shown, for example in FIGS. 17-24. Here, the home medication management system includes a base having a docking station (e.g.) 1700 as shown, for example, in FIG. 17 and a removable tote portion (e.g., 1700a) as exemplified in FIG. 18. As shown by FIGS. 17 and 18, the components within the docking station 1700 and components within the removable tote portion 1700a can communicate with each other via the I/O Port 600 in the docking station 1700 and I/O Port 600a in the removable tote portion 1700. Additionally, certain components of the removable tote portion 1700a can receive power from the docking station via the Input Power Supply 601a and Output Power Supply 601. For example, power can be supplied from the docking station 1700 to the removable tote portion 1700a using conduction. Two electrical contacts are disposed on an internal surface of the docking station 1700. The two electrical contacts serve as the Output Power Supply 601. In an aspect of the disclosure, the two electrical contacts are located on the bottom internal surface of the docketing station 1700. Two electrical contacts are also disposed on an external surface of the removable tote portion 1700a. In an aspect of the disclosure, the two electrical contacts are located on the bottom external surface of the removal tote portion 1700a and correspond to the location of the two electrical contacts on the docking station 1700. When the removable tote portion 1700a is in the docking station 1700 the respective electrical contacts touch each other. The two electrical contacts on the removable tote portion 1700a serve as the Input Power Supply 601.

The Output Power Supply 601 receives power under the control of the Controller 206. When the Output Power Supply 601 receives power, the power is conducted to the Input Power Supply 601 due to the direct contact of the respective electrical contacts. The power that is conducted to the Input Power Supply is then used to supply power to the sensors 212 and other electrical components of the removable tote portion 1700a including the RFID chip 500.

In one embodiment of the disclosure, the respective electrical contacts can also serve as the I/O Ports 600/600a. Data can be modulated at a specific frequency. The modulated output can be evaluated by a Controller 206 to determine the data, as described below in further detail.

In another embodiment of the disclosure, one or more electrical connectors can be used to transfer data and power between components within the docking station 1700 and components within the removable tote portion. For example, USB connection can be used. In an aspect of the disclosure, a female receptacle for the USB connector is disposed on an internal surface of the docking station 1700, A male USB connector is disposed on the external surface of the portable tote portion 1700a in a corresponding location to mate with the female receptacle on the docking station 1700. For example, the male USB connector is located on the bottom external surface of the portable tote portion 1700a and the female receptacle is located on the bottom internal surface of the docking station 1700. When the portable tote portion 1700a is in the docketing station 1700, the male USB connector mates with the female receptacle.

Using the USB connection, both power and data can be transferred using the same connector. Different ports within the male USB connector are used to transfer power and data. Thus, the male USB connector can serve as both the I/O Data Port 600a and the Input Power Supply 601a. Additionally, the female receptacle can serve as both the I/O Data Port 600 and the Output Power Supply 601.

Other electrical connectors can be used such as, but not limited to, a 8, 9, 25 or 30-pin connector and corresponding female receptacle. Certain pin(s) can be used to transfer power and other pins can be used to transmit or receive data. The male portion of the connector can be disposed on the bottom external surface of the removable tote portion and the female receptacle can be disposed in a corresponding location of the bottom internal surface of the docking station.

In another aspect of the disclosure, power and data can be transmitted wirelessly or via a non-contact delivery method. FIGS. 21-24 depict embodiments where the transfer of power and data are wirelessly or non-contact. For example, inductive power and data transmission can be used. Inductive power and data would be transferred from the docking station 1800/1900 using a tuned inductor and resonant resistor. The inductor and resonant resistor can serve as the Wireless Power Antenna 611. The removable tote portion 1800a/1900a would have a corresponding resonant circuit having an inductor and resonant resistor. The inductor and resonant resistor is tuned to resonate at substantially the same resonant frequency as the tuned inductor and resonant resistor in the docking station. The corresponding resonant circuit, e.g., inductor and resonant resistor, can serve as the Wireless Power Antenna 611a.

The controller 206 controls the power supplied to the Wireless Power Antenna to regulate the induced power and transmitted data. Similarly, the two resonant circuits can serve as the Wireless Antenna I/O Data 610/610a. The controller 206 can transmit data to the removable tote portion 1800a/1900a using the resonant circuits. Similarly, data transmitted from the removable tote portion 1800a/1900a transmitted under the control of the Controller 206a present in the removable tote portion.

Figure 21:
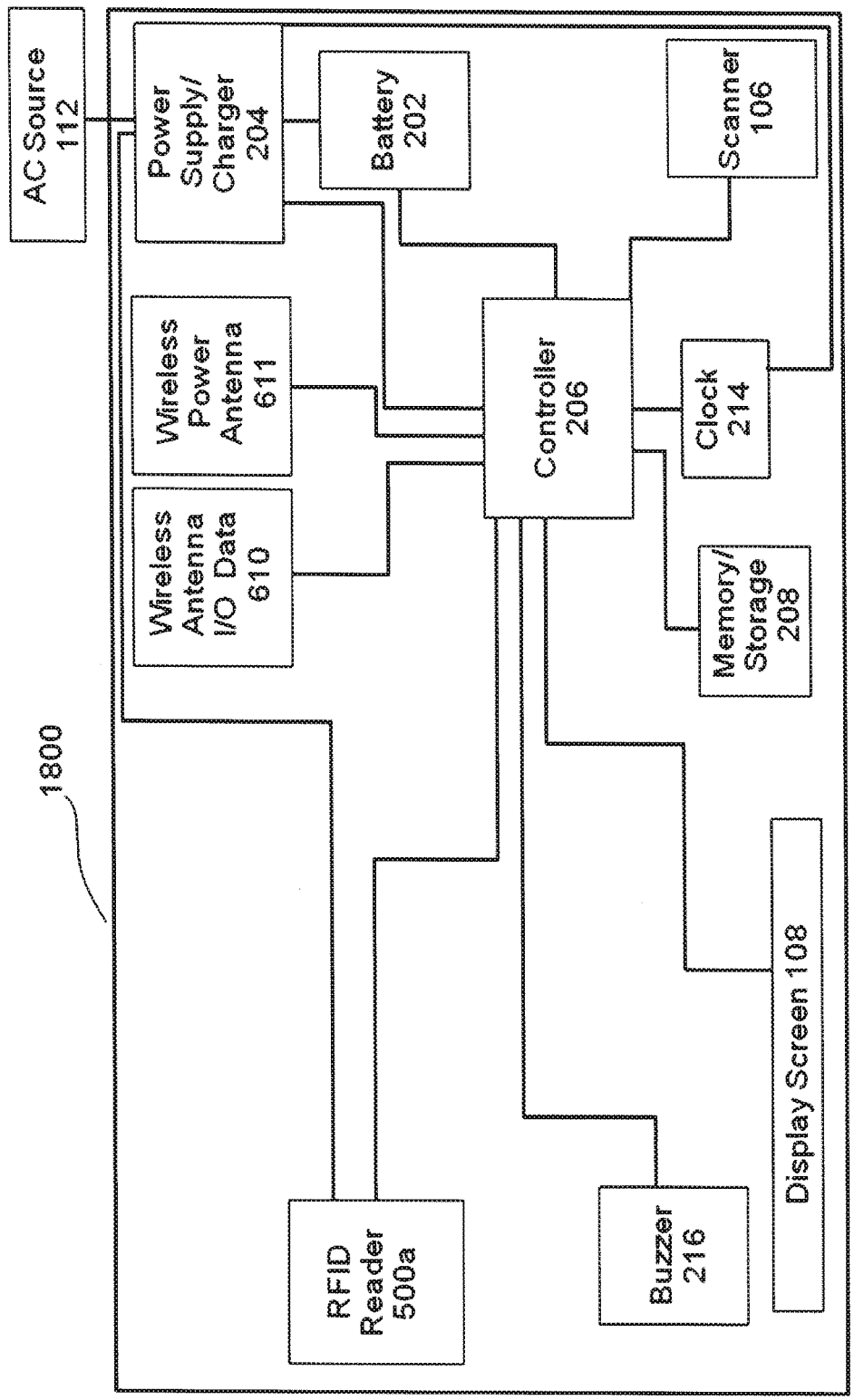
FIGS. 21-22 illustrate block representations of an embodiment of the present disclosure including a base unit having a removable tote element and a docking station.
Figure 22:
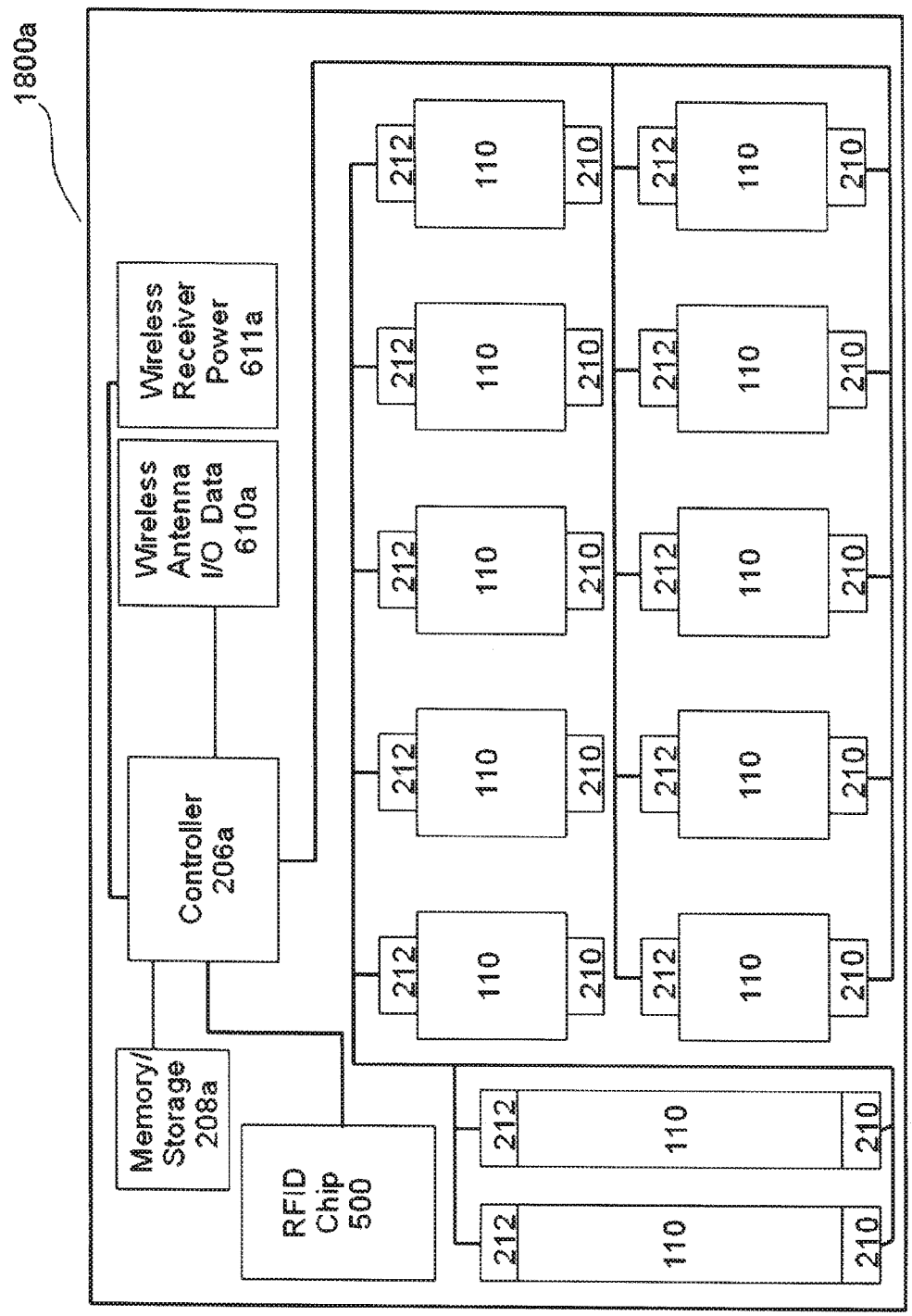
Figure 23:
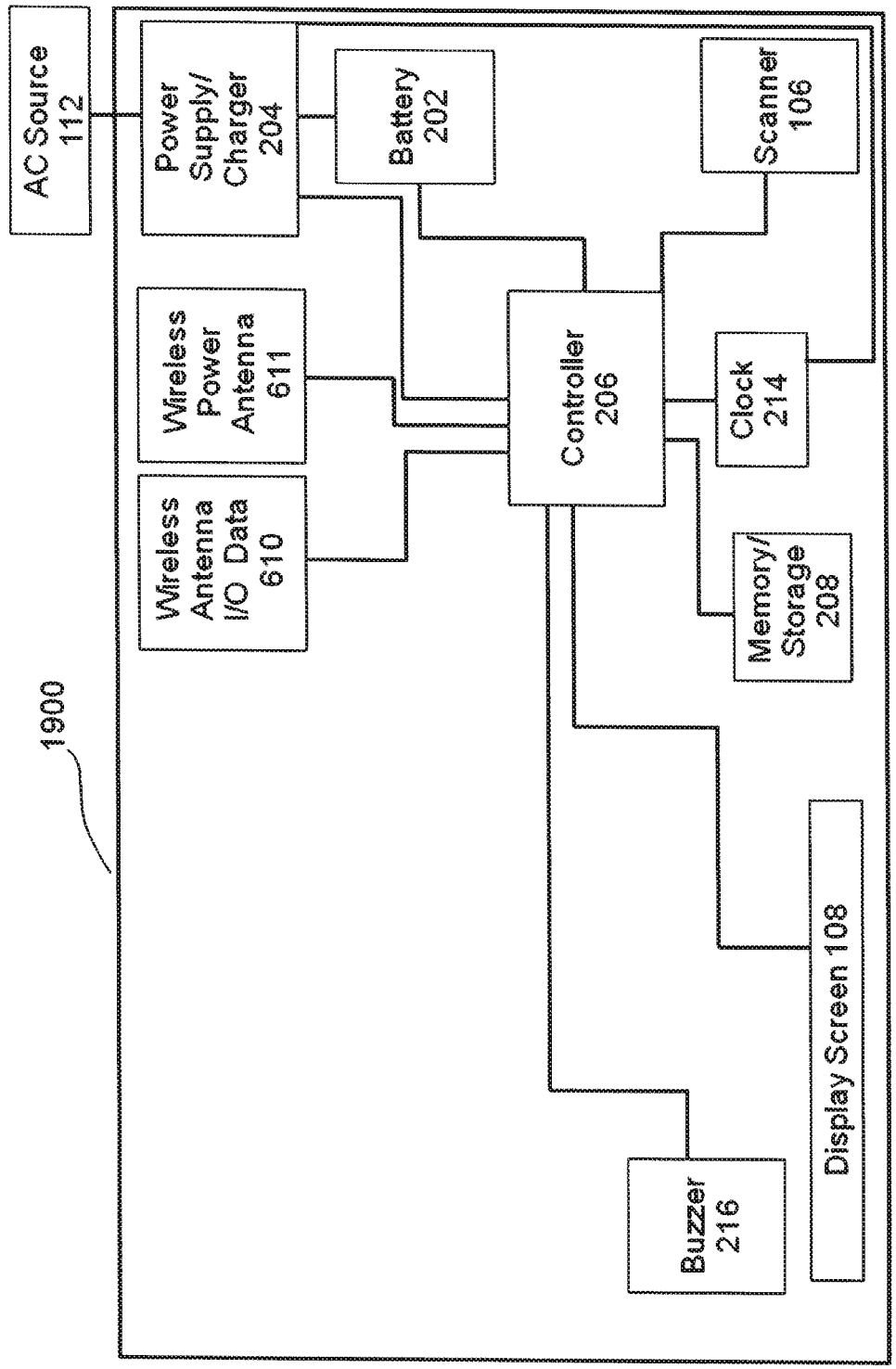
FIGS. 23-24 illustrate block representations of an embodiment of the present disclosure including a base unit having a removable tote element and a docking station.
Figure 24:
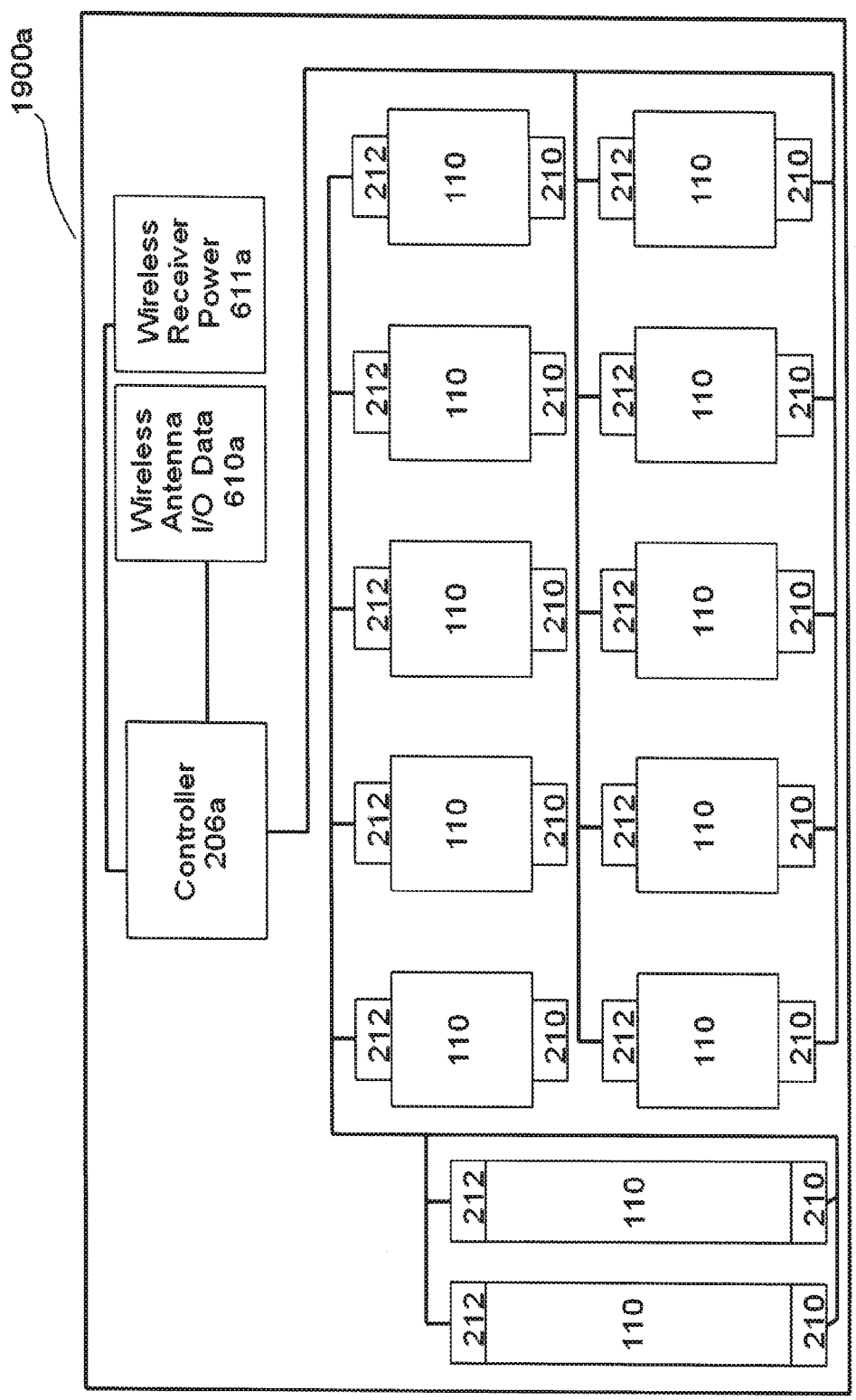

As shown in FIGS. 21-22, in a specific embodiment, the home medication manager can have a hardware processor or controller 206/206a, such as a microcontroller or Field Programmable Gate Array (FPGA), which can perform various operations. The controller 206/206a can execute instructions as described below. These instructions can be stored, for example, on a memory device and/or computer readable medium, such as a computer readable storage device 208/208a. The computer readable media may be any available non-transitory media that is accessible by computer system, and it may include both volatile and non-volatile media, and removable and non-removable media, such as random access memory (RAM) and/or cache memory or others. A hardwire network connection can be provided to the controller to allow for data transfer and/or software upgrades. In addition, or in the alternative, wi-fi can be included to enable the controller to connect with one or more external sources. In one embodiment, the controller can communicate with smartphones and/or tablets, as well as a wrist band and/or pendant 300, and/or a compact electronic box 1401.

The controller 206, located in the docking station can control scanning of the original medication container by the scanner 106 and can provide instructions and/or alerts through the one or more display screens 108/1001. Additionally, controller 206, located in the docking station can communicate data with a second controller 206a located in the removable tote portion of the base through, for example, the Wireless Data Antenna 610/610a, an I/O Data Port 600/600a, or an RFID reader 500a.

For example, when scanning an original medication container, the controller 206 in the docking station 1800 can determine whether the medication is a new medication or a refill by referencing information stored in the memory/storage device 208. In one embodiment, a database of current managed medications, is stored in the memory/storage device 208 in the docking station and another memory/storage device 208a in the removable tote portion. New medication can be added to this database or to other data stored in a memory/storage device 208/208a. Additional information regarding the scanned medication, such as usage instructions, number of refills and expiration date can be acquired from, for example, interaction with a pharmacy database, or cloud based network of remote servers ("cloud database") the indicia scanned from the original medication container, if available, or through interaction with the patient/user via the display screen 108. This information can be stored in the database of current managed medications, as well on a pharmacy database, if applicable.

A controller 206/206a can also select an available receptacle 110a to receive new or refill original medication container(s) and can indicate the selection by illuminating a light (e.g., LED) 210, as shown, for example, in FIG. 2, which is associated with the selected receptacle 110a. A sensor 212, such as photodiode and LED assembly, disposed inside each of the receptacles 110a can be triggered when the original medication container is received by the selected receptacle 110a. Other sensors, as known to one skilled in the art, can also be used. The trigger of the sensor is communicated to (i.e., received by) the controller 206/206a which verifies that the original medication container has been placed in the correct receptacle 110a. The controller 206/206a can associate the receptacle assignment, e.g., location, with the medication held in the original medication container and stored in the assigned receptacle, e.g., location, in the database of current managed medications.

In a specific embodiment, notification to take a medication occurs when the home medication management system communicates through a memory/storage device 208/208a, controller 206/206a, Wireless Data Antenna 610/610a, Data I/O Port 600/600a, wi-fi or Bluetooth to alert the patient, e.g., through a cell phone, tablet or smart phone, causing the cell phone or smart phone to ring and/or vibrate. Other notification means can also be used. For example, the controller 206/206a can activate the LED 210 corresponding to the receptacle 110a holding the medication to be taken. If the patient inadvertently retrieves a medication from the incorrect receptacle 110a, the controller 206/206a can detect the occurrence by way of the sensor 212 associated with improper receptacle 100a and can display a warning message on the display screen 108a and/or can sound an alert by way of the buzzer 216 and/or the speaker 114. In another embodiment, when it is time for a medication to be taken, the patient can be notified by a notification means such as a buzzer 216, which in certain embodiments may provide a vibrating alert to the user, or short range wireless communication provided by a wireless communication circuit 218, such as Bluetooth, in communication with a portable electronic device including, for example, a paired bracelet, e.g., wrist alert, or fob, which can be worn, for example, as a pendant 300, a cell phone, smart phone, tablet or software application thereof, or any other Bluetooth or wi-fi compatible device know to one of ordinary skill in the art. In one specific embodiment, the notification can occur when the bracelet or pendant 300 lights up and/or vibrates.

In the case where the medication must be refrigerated, and thus not held in one of the receptacles 110, the controller 206/206a can provide instructions on the display screen 108 to retrieve the medication from the refrigerator and can scan the barcode of the original medication container prior to administration. Scanning the barcode of the refrigerated original medication container prior to administration allows the controller 206/206a to verify that the correct medication is being taken.

Retrieval of the correct medication from the indicated receptacle 110a can be detected by the controller 206/206a by way of the sensor 212. The controller 206 can record the time and date of the dosing in a database stored in the memory/storage device 208/208a. This database can be the same as the database of current managed medications or can be a separate database, such as a pharmacy database. In one embodiment, the data can be stored on an external device, such as a server, cloud database, and/or portable electronic device (e.g., cell phone, tablet and/or smartphone).

The controller 206/206a may provide further instructions, such as instructing the patient to take a certain number of pills or amount of liquid medication, to take the medication with food, or refrain from eating for a period after taking the medication. The instructions can be provided via the speaker 114, and/or a display screen 108, and/or a wrist alert, or fob, which can be worn, for example, as a pendant 300, a cell phone, smartphone, tablet or software application thereof.

The wireless circuit 218/218a can include multiple communication protocols, such as Bluetooth, 802.11a/b/g/n, and CDMA, GSM and 3G/4G/4G LTE mobile phone communication protocols. 802.11a/b/g/n and mobile phone communication protocols can be utilized by the controller 206/206a to contact a medication database service (e.g., pharmacy database or cloud database) for retrieving medication information relating to drug interactions, administering information, etc. The wireless circuit 218/218a can allow the controller 206/206a to contact a treating health organization to relay medication compliance information and other related information for the patient's health records. The controller 206/206a can be configured to provide encryption and decryption when sending or receiving personal health-related information in order to maintain patient privacy; in one embodiment the data will be HIPAA (Health Insurance Portability and Accountability Act) compatible. In one embodiment, the controller 206/206a can allow sharing of data regarding compliance, errors, device malfunction; in addition, the controller can perform updates and changes to the current therapy. In a specific embodiment, the controller shares stored data related to the amount of a particular medication being managed by the home medication device with a pharmacy database or other external database (e.g., cloud database).

In another aspect of the disclosure, power and data can be separately transmitted. For example, power can be transmitted as described above; however, the data can be transmitted using wireless antennas implementing different wireless protocols.

In another aspect of the disclosure, instead of having a separate Wireless Antenna 610/611, an RFID Reader can be used to transfer power to and data to and from the removable tote portion, e.g., to an RFID Tag 500.

In one embodiment, the base housing of the home medication manager can contain a Compact Flash Memory Card (not shown), operable in a memory card slot 902, which will record all activity that the manager performs. This card can be hot swappable and the manager will function with or without it. In one embodiment, the card can hold over a year's worth of data. When the new patient option is selected, the data can be automatically erased.

In one embodiment, the inventive method described herein may be implemented as hardware on a reconfigurable hardware, e.g., FPGA (Field Programmable Gate Array) or CPLD (Complex Programmable Logic Device), by using a hardware description language (e.g., Verilog, VHDL, Handel-C, or System C). In another embodiment, the inventive method may be implemented on a semiconductor chip, e.g., ASIC (Application-Specific Integrated Circuit), by using a semi custom design methodology, i.e., designing a semiconductor chip using standard cells and a hardware description language.

The computer system may be any type of known or will be known systems and may typically include a processor, memory device, a storage device, input/output devices, internal buses, and/or a communications interface for communicating with other computer systems in conjunction with communication hardware and software, etc. Portions of the system also may be implemented on a virtual computer system, colloquially known as a cloud.

Regarding a computer readable storage medium, it may be, for example, a magnetic, optical, electronic, electromagnetic, infrared, or semiconductor system, apparatus, or device, or any suitable combination of the foregoing; however, the computer readable storage medium is not limited to these examples. Additional particular examples of the computer readable storage medium can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an electrical connection having one or more wires, an optical fiber, an optical storage device, or any appropriate combination of the foregoing; however, the computer readable storage medium is also not limited to these examples. Any tangible medium that can contain, or store a program for use by or in connection with an instruction execution system, apparatus, or device could be a computer readable storage medium.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A self medication management apparatus comprising:
    a removable tote comprising a plurality of receptacles, where each receptacle has at least a sensor and an associated visual indicator, wherein said plurality of receptacles are capable of housing individual unaltered medication containers, and wherein said removable tote further comprises a continuous bottom external surface interspersed between a bottom surface of the unaltered medication containers and a top surface of a docking station;
    said docking station comprising:
        a power supply;
        a storage device; and
        a processor comprising hardware configured to:
            acquire medication information from an unaltered medication container holding a medication, the medication information comprising at least an administration time;
            determine whether the medication information exists in a first database residing on the storage device;
            if the medication information does not exist in the first database, associate the medication information with location information identifying a receptacle of said plurality of receptacles and store the medication information and the location information in the first database;
            indicate, using the visual indicator corresponding to the associated receptacle of said plurality of receptacles and the location information, placement of the unaltered medication container in the associated receptacle;
            notify a user to administer the medication held in the unaltered medication container based on the administration time;
            detect retrieval of an incorrect unaltered medication container from the plurality of receptacles, and issue a warning of the detection; and
            provide instructions for administering the medication, wherein the instructions are based on the medication information.

2. The self medication management apparatus of claim 1, wherein the processor further comprises hardware configured to track administering of the medications in a second database residing on the storage device.

3. The self medication management apparatus of claim 2, wherein the processor is further configured to send information from the second database to an external source.

4. The self medication management apparatus of claim 3, wherein the external source is a pharmacy database or cloud database.

5. The self medication management apparatus of claim 2, wherein the processor further comprises hardware configured to acquire additional medication information from an external source.

6. The self medication management apparatus of claim 5, wherein the external source is a pharmacy database or cloud database.

7. The self medication management apparatus of claim 1, wherein the processor further comprises hardware configured to receive medication from a smartphone and transmit medication information to said smartphone.

8. The self medication management apparatus of claim 1, wherein said visual indicator comprises a light emitting diode (LED).

9. The self medication management apparatus of claim 1, wherein the docking station further comprises a first communication section; and wherein the removable tote further comprises a second communication section, wherein when the removable tote is placed in the docking station such that the first communication section and the second communication section are capable of communicating with each other.

10. The self medication management apparatus of claim 9, wherein the first communication section and the second communication section are wireless communication devices.

11. The self medication management apparatus of claim 1, wherein the docking station further comprises a buzzer, and wherein said buzzer provides a notification to the user to administer the medication.

12. The self medication management apparatus of claim 1, wherein the docking station further comprises a speaker, and wherein said speaker provides an audible notification to the user to administer the medication and said instructions for administering the medication.

13. The self medication management apparatus of claim 1, wherein the docking station further comprises a power transmitting section; and wherein the removable tote further comprises a power reception section and wherein when the removable tote is placed in the docking station, the power transmitting section is capable of transmitting power to the removable tote via the power reception section.

14. The self medication management apparatus of claim 13, wherein the power is wirelessly transmitted from the docking station to the removable tote.

15. The self medication management apparatus of claim 13, wherein the power is inductively transmitted from the power transmitting section to the power reception section.

16. The self medication management apparatus of claim 13, wherein the power transmitting section and power reception section respectively comprise electric contacts, and wherein when the removable tote is placed in the docking station, power is capable of being conducted via direct contact between electric contacts, respectively in the docking station and removable tote.

17. The self medication management apparatus of claim 1, wherein said sensor is located within each receptacle of said plurality of receptacles.

18. The self medication management apparatus of claim 1, wherein said plurality of receptacles is 12 to 20 receptacles.

19. The self medication management apparatus of claim 18, wherein said plurality of receptacles is 12 receptacles.

20. The self medication management apparatus of claim 18, wherein said plurality of receptacles is 20 receptacles.

* * * * *